United States Patent
Bar-Tana

(10) Patent No.: US 10,512,624 B2
(45) Date of Patent: Dec. 24, 2019

(54) LONG-CHAIN AMPHIPATHIC DICARBOXYLIC ACIDS FOR TREATMENT OF DIABETES TYPE-1

(71) Applicant: Syndromex Ltd., Jerusalem (IL)

(72) Inventor: Jacob Bar-Tana, Jerusalem (IL)

(73) Assignee: SYNDROMEX LTD., Jerusalem (IL)

( * ) Notice: Subject to any disclaimer, the term of this patent is extended or adjusted under 35 U.S.C. 154(b) by 0 days.

(21) Appl. No.: 15/827,121

(22) Filed: Nov. 30, 2017

(65) Prior Publication Data

US 2018/0235918 A1 Aug. 23, 2018

Related U.S. Application Data

(60) Provisional application No. 62/427,923, filed on Nov. 30, 2016.

(51) Int. Cl.
*A61K 31/20* (2006.01)
*A61P 3/10* (2006.01)

(52) U.S. Cl.
CPC ............... *A61K 31/20* (2013.01); *A61P 3/10* (2018.01)

(58) Field of Classification Search
CPC .................................................... A61K 31/225
See application file for complete search history.

(56) References Cited

U.S. PATENT DOCUMENTS

2009/0018199 A1* 1/2009 Bar-Tana et al.

FOREIGN PATENT DOCUMENTS

| WO | 8600298 A1 | 1/1986 | |
|---|---|---|---|
| WO | 9830530 A1 | 7/1998 | |
| WO | WO-9830530 A1 * | 7/1998 | ............. C07C 55/02 |

OTHER PUBLICATIONS

Kaul et al., Metabolism, 2015;64:1629-1639 (Year: 2015).*
Himsworth HP. Management of Diabetes Mellitus. Br Med J. 1936;2(3941):137-41.
Schauer IE, Snell-Bergeon JK, Bergman BC, Maahs DM, Kretowski A, Eckel RH, and Rewers M. Insulin resistance, defective insulin-mediated fatty acid suppression, and coronary artery calcification in subjects with and without type 1 diabetes: The CACTI study. Diabetes. 2011; 60(1):306-14.
Chaparro RJ, Konigshofer Y, Beilhack GF, Shizuru JA, McDevitt HO, and Chien YH. Nonobese diabetic mice express aspects of both type 1 and type 2 diabetes. Proc Natl Acad Sci U S A. 2006;103(33):12475-80.
Hong EG, Jung DY, Ko HJ, Zhang Z, Ma Z, Jun JY, Kim JH, Sumner AD, Vary TC, Gardner TW, et al. Nonobese, Insulin-deficient Ins2Akita mice develop type 2 diabetes phenotypes including insulin resistance and cardiac remodeling. Am J Physiol Endocrinol Metab. 2007;293(6):E1687-96.

(Continued)

*Primary Examiner* — San Ming R Hui
(74) *Attorney, Agent, or Firm* — Browdy and Neimark, PLLC

(57) ABSTRACT

Disclosed are methods of treatment of type 1 diabetes (T1D) in subjects under standard-of-care T1D treatment, by administration of substituted long-chain amphipathic dicarboxylic acids. Also disclosed are methods of reducing standard-of-care administered dose of insulin or an insulin analogue and/or obviating the need for administration of insulin or an insulin analogue in a T1D subject by administration of substituted long-chain amphipathic dicarboxylic acids.

26 Claims, 16 Drawing Sheets

Specification includes a Sequence Listing.

(56) References Cited

OTHER PUBLICATIONS

Fourlanos S, Narendran P, Byrnes GB, Colman PG, and Harrison LC. Insulin resistance is a risk factor for progression to type 1 diabetes. Diabetologia. 2004;47(10):1661-7.
Jelenik T, Séquaris G, Kaul K, Ouwens DM, Phielix E, Kotzka J, Knebel B, Weiß J, Reinbeck AL, Janke L, et al. Tissue-specific differences in the development of insulin resistance in a mouse model for type 1 diabetes. Diabetes. 2014;63(11):3856-67.
Brooks-Worrell B, Narla R, and Palmer JP. Islet autoimmunity in phenotypic type 2 diabetes patients. Diabetes Obes Metab. 2013;15 Suppl 3(137-40).
Basile KJ, Guy VC, Schwartz S, and Grant SF. Overlap of genetic susceptibility to type 1 diabetes, type 2 diabetes, and latent autoimmune diabetes in adults.Curr Diab Rep. 2014;14(11):550.
Wilkin TJ. The convergence of type 1 and type 2 diabetes in childhood: the accelerator hypothesis. Pediatr Diabetes. 2012;13(4):334-9.
Beales PE, Giorgini A, Annovazzi A, Signore A, Parlapiano C, and Pozzilli P. Metformin does not alter diabetes incidence in the NOD mouse. Horm Metab Res. 1997;29(6):261-3.
Beales PE, Liddi R, Giorgini AE, Signore A, Procaccini E, Batchelor K, and Pozzilli P. Troglitazone prevents insulin dependent diabetes in the non-obese diabetic mouse. Eur J Pharmacol. 1998;357(2-3):221-5.
Liu C, Wu D, Zheng X, Li P, and Li L. Efficacy and safety of metformin for patients with type 1 diabetes mellitus: a meta-analysis. Diabetes Technol Ther. 2015;17(2):142-8.
Shimada A, Shigihara T, Okubo Y, Katsuki T, Yamada Y, and Oikawa Y. Pioglitazone may accelerate disease course of slowly progressive type 1 diabetes. Diabetes Metab Res Rev. 2011;27(8):951-3.
Tafuri KS, Godil MA, Lane AH, and Wilson TA. Effect of pioglitazone on the course of new-onset type 1 diabetes mellitus. J Clin Res Pediatr Endocrinol. 2013;5(4):236-9.
Bar-Tana J, Ben-Shoshan S, Blum J, Migron Y, Hertz R, Pill J, Rose-Khan G, and Witte EC. Synthesis and hypolipidemic and antidiabetogenic activities of beta,beta,beta',beta'- tetrasubstituted, long-chain dioic acids. J Med Chem. 1989;32(9):2072-84.
Zatara G, Hertz R, Shaked M, Mayorek N, Morad E, Grad E, Cahan A, Danenberg HD, Unterman TG, and Bar-Tana J. Suppression of FoxO1 activity by long-chain fatty acyl analogs. Diabetes. 2011;60(7):1872-81.
Za'tara G, Bar-Tana J, Kalderon B, Suter M, Morad E, Samovski D, Neumann D, and Hertz R. AMPK activation by long chain fatty acyl analogs. Biochem Pharmacol. 2008;76(10):1263-75.
Russell JC, Shillabeer G, Bar-Tana J, Lau DC, Richardson M, Wenzel LM, Graham SE, and Dolphin PJ. Development of insulin resistance in the JCR:LA-cp rat: role of triacylglycerols and effects of MEDICA 16. Diabetes. 1998;47(5):770-8.
Mayorek N, Kalderon B, Itach E, and Bar-Tana J. Sensitization to insulin induced by beta,beta'-methyl-substituted hexadecanedioic acid (MEDICA 16) in obese Zucker rats in vivo. Diabetes. 1997;46(12)1958-64.
Russell JC, Amy RM, Graham SE, Dolphin PJ, Wood GO, and Bar-Tana J. Inhibition of atherosclerosis and myocardial lesions in the JCR:LA-cp rat by beta, beta'- tetramethylhexadecanedioic acid (MEDICA 16). Arterioscler Thromb Vasc Biol. 1995;15(7):918-23.
Lind M, Svensson AM, Kosiborod M, Gudbjörnsdottir S, Pivodic A, Wedel H, Dahlqvist S, Clements M, and Rosengren A. Glycemic control and excess mortality in type 1 diabetes. N Engl J Med. 2014;371(21):1972-82.
Cleland SJ. Cardiovascular risk in double diabetes mellitus—when two worlds collide. Nat Rev Endocrinol. 2012;8(8):476-85.
Brown RJ, and Rother KI. Effects of beta-cell rest on beta-cell function: a review of clinical and preclinical data. Pediatr Diabetes. 2008;9(3 Pt 2):14-22.
Oram RA, Jones AG, Besser RE, Knight BA, Shields BM, Brown RJ, Hattersley AT, and McDonald TJ. The majority of patients with long-duration type 1 diabetes are insulin microsecretors and have functioning beta cells. Diabetologia. 2014;57(1):187-91.
Wang L, Lovejoy NF, and Faustman DL. Persistence of prolonged C-peptide production in type 1 diabetes as measured with an ultrasensitive C-peptide assay. Diabetes Care. 2012;35(3):465-70.
Ayala JE, Bracy DP, Malabanan C, James FD, Ansari T, Fueger PT, McGuinness OP, and Wasserman DH. Hyperinsulinemic-euglycemic clamps in conscious, unrestrained mice. J Vis Exp. 201157) (2011).
Altarejos JY, and Montminy M. CREB and the CRTC co-activators: sensors for hormonal and metabolic signals. Nat Rev Mol Cell Biol. 2011;12(3):141-51.
Kalderon B, Azazmeh N, Azulay N, Vissler N, Valitsky M, and Bar-Tana J. Suppression of adipose lipolysis by long-chain fatty acid analogs. J Lipid Res. 2012;53(5):868-78.
Kramer HF, Witczak CA, Fujii N, Jessen N, Taylor EB, Arnolds DE, Sakamoto K, Hirshman MF, and Goodyear LJ. Distinct signals regulate AS160 phosphorylation in response to insulin, AICAR, and contraction in mouse skeletal muscle. Diabetes. 2006; 55(7):2067-76.

* cited by examiner

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcatcttggt gtccgtgatc g         21

<210> SEQ ID NO 2
<211> LENGTH: 21
<212> TYPE: DNA

```
<213> ORGANISM: Artificial Sequence
<220> FEATURE:
<223> OTHER INFORMATION: Synthetic

<400> SEQUENCE: 2
tttatcaggg gcacggaagt g                                            21

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
ggccacagct gctgcag                                                 17

<210> SEQ ID NO 4
<211> LENGTH: 17
<212> TYPE: DNA
<213> ORGANISM: Artificial Sequence
<220> FEATURE:
<223> OTHER INFORMATION: Synthetic

<400> SEQUENCE: 4
ggtcgcatgg caaaggg                                                 17

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tagcagagat caccaatgcc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ggcagcaagc catgtattta                                              20
```

LONG-CHAIN AMPHIPATHIC DICARBOXYLIC ACIDS FOR TREATMENT OF DIABETES TYPE-1

The Sequence Listing in ASCII text file format of 1,397 bytes in size, created on Feb. 8, 2018, with the file name "2018-02-15SequenceListing_BAN-TANA8," filed in the U.S. Patent and Trademark Office on Feb. 15, 2018, is hereby incorporated herein by reference.

TECHNOLOGICAL FIELD

The presently disclosed subject matter relates to long-chain α,ω-dicarboxylic acid compounds and pharmaceutical compositions comprising thereof for use in the treatment of type 1 diabetes (T1D). In one of its aspects the disclosure relates to combined treatment of T1D with long-chain α,ω-dicarboxylic acid compounds and insulin.

BACKGROUND ART

References considered to be relevant as background to the presently disclosed subject matter are listed below:

REFERENCES

1. Himsworth H P. MANAGEMENT OF DIABETES MELLITUS. Br Med J. 1936; 2(3941):137-41.
2. Schauer I E, Snell-Bergeon J K, Bergman B C, Maahs D M, Kretowski A, Eckel R H, and Rewers M. Insulin resistance, defective insulin-mediated fatty acid suppression, and coronary artery calcification in subjects with and without type 1 diabetes: The CACTI study. Diabetes. 2011; 60(1):306-14.
3. Chaparro R J, Konigshofer Y, Beilhack G F, Shizuru J A, McDevitt H O, and Chien Y H. Nonobese diabetic mice express aspects of both type 1 and type 2 diabetes. Proc Natl Acad Sci USA. 2006; 103(33):12475-80.
4. Hong E G, Jung D Y, Ko H J, Zhang Z, Ma Z, Jun J Y, Kim J H, Sumner A D, Vary T C, Gardner T W, et al. Nonobese, insulin-deficient Ins2Akita mice develop type 2 diabetes phenotypes including insulin resistance and cardiac remodeling. Am J Physiol Endocrinol Metab. 2007; 293(6):E1687-96.
5. Fourlanos S, Narendran P, Byrnes G B, Colman P G, and Harrison L C. Insulin resistance is a risk factor for progression to type 1 diabetes. Diabetologia. 2004; 47(10):1661-7.
6. Jelenik T, Séquaris G, Kaul K, Ouwens D M, Phielix E, Kotzka J, Knebel B, Weiß J, Reinbeck A L, Janke L, et al. Tissue-specific differences in the development of insulin resistance in a mouse model for type 1 diabetes. Diabetes. 2014; 63(11):3856-67.
7. Brooks-Worrell B, Narla R, and Palmer J P. Islet autoimmunity in phenotypic type 2 diabetes patients. Diabetes Obes Metab. 2013; 15 Suppl 3(137-40).
8. Basile K J, Guy V C, Schwartz S, and Grant S F. Overlap of genetic susceptibility to type 1 diabetes, type 2 diabetes, and latent autoimmune diabetes in adults. Curr Diab Rep. 2014; 14(11):550.
9. Wilkin T J. The convergence of type 1 and type 2 diabetes in childhood: the accelerator hypothesis. Pediatr Diabetes. 2012; 13 (4):334-9.
10. Beales P E, Giorgini A, Annovazzi A, Signore A, Parlapiano C, and Pozzilli P. Metformin does not alter diabetes incidence in the NOD mouse. Horm Metab Res. 1997; 29(6):261-3.
11. Beales P E, Liddi R, Giorgini A E, Signore A, Procaccini E, Batchelor K, and Pozzilli P. Troglitazone prevents insulin dependent diabetes in the non-obese diabetic mouse. Eur J Pharmacol. 1998; 357(2-3):221-5.
12. Liu C, Wu D, Zheng X, Li P, and Li L. Efficacy and safety of metformin for patients with type 1 diabetes mellitus: a meta-analysis. Diabetes Technol Ther. 2015; 17(2):142-8.
13. Shimada A, Shigihara T, Okubo Y, Katsuki T, Yamada Y, and Oikawa Y. Pioglitazone may accelerate disease course of slowly progressive type 1 diabetes. Diabetes Metab Res Rev. 2011; 27(8):951-3.
14. Tafuri K S, Godil M A, Lane A H, and Wilson T A. Effect of pioglitazone on the course of new-onset type 1 diabetes mellitus. J Clin Res Pediatr Endocrinol. 2013; 5(4): 236-9.
15. Bar-Tana J, Ben-Shoshan S, Blum J, Migron Y, Hertz R, Pill J, Rose-Khan G, and Witte E C. Synthesis and hypolipidemic and antidiabetogenic activities of beta, beta,beta',beta'-tetrasubstituted, long-chain dioic acids. J Med Chem. 1989; 32(9):2072-84.
16. Zatara G, Hertz R, Shaked M, Mayorek N, Morad E, Grad E, Cahan A, Danenberg H D, Unterman T G, and Bar-Tana J. Suppression of FoxO1 activity by long-chain fatty acyl analogs. Diabetes. 2011; 60(7):1872-81.
17. Za'tara G, Bar-Tana J, Kalderon B, Suter M, Morad E, Samovski D, Neumann D, and Hertz R. AMPK activation by long chain fatty acyl analogs. Biochem Pharmacol. 2008; 76(10): 1263-75.
18. Russell J C, Shillabeer G, Bar-Tana J, Lau D C, Richardson M, Wenzel L M, Graham S E, and Dolphin P J. Development of insulin resistance in the JCR:LA-cp rat: role of triacylglycerols and effects of MEDICA 16. Diabetes. 1998; 47(5):770-8.
19. Mayorek N, Kalderon B, Itach E, and Bar-Tana J. Sensitization to insulin induced by beta,beta'-methyl-substituted hexadecanedioic acid (MEDICA 16) in obese Zucker rats in vivo. Diabetes. 1997; 46(12):1958-64.
20. Russell J C, Amy R M, Graham S E, Dolphin P J, Wood G O, and Bar-Tana J. Inhibition of atherosclerosis and myocardial lesions in the JCR:LA-cp rat by beta, beta'-tetramethylhexadecanedioic acid (MEDICA 16). Arterioscler Thromb Vasc Biol. 1995; 15(7):918-23.
21. WO1986/000298
22. WO1998/30530
23. Lind M, Svensson A M, Kosiborod M, Gudbjörnsdottir S, Pivodic A, Wedel H, Dahlqvist S, Clements M, and Rosengren A. Glycemic control and excess mortality in type 1 diabetes. N Engl J Med. 2014; 371(21):1972-82.
24. Cleland S J. Cardiovascular risk in double diabetes mellitus—when two worlds collide. Nat Rev Endocrinol. 2012; 8(8):476-85.
25. Brown R J, and Rother K I. Effects of beta-cell rest on beta-cell function: a review of clinical and preclinical data. Pediatr Diabetes. 2008; 9(3 Pt 2):14-22.
26. Oram R A, Jones A G, Besser R E, Knight B A, Shields B M, Brown R J, Hattersley A T, and McDonald T J. The majority of patients with long-duration type 1 diabetes are insulin microsecretors and have functioning beta cells. Diabetologia. 2014; 57(1):187-91.
27. Wang L, Lovejoy N F, and Faustman D L. Persistence of prolonged C-peptide production in type 1 diabetes as measured with an ultrasensitive C-peptide assay. Diabetes Care. 2012; 35(3):465-70.
28. Ayala J E, Bracy D P, Malabanan C, James F D, Ansari T, Fueger P T, McGuinness O P, and Wasserman D H.

Hyperinsulinemic-euglycemic clamps in conscious, unrestrained mice. J Vis Exp. 201157).
29. Altarejos J Y, and Montminy M. CREB and the CRTC co-activators: sensors for hormonal and metabolic signals. Nat Rev Mol Cell Biol. 2011; 12(3):141-51.
30. Kalderon B, Azazmeh N, Azulay N, Vissler N, Valitsky M, and Bar-Tana J. Suppression of adipose lipolysis by long-chain fatty acid analogs. J Lipid Res. 2012; 53(5): 868-78.
31. Kramer H F, Witczak C A, Fujii N, Jessen N, Taylor E B, Arnolds D E, Sakamoto K, Hirshman M F, and Goodyear L J. Distinct signals regulate AS160 phosphorylation in response to insulin, AICAR, and contraction in mouse skeletal muscle. Diabetes. 2006; 55(7):2067-76.

Acknowledgement of the above references herein is not to be inferred as meaning that these are in any way relevant to the patentability of the presently disclosed subject matter.

BACKGROUND

Diabetes mellitus type 1 (also known inter alia as type 1 diabetes, or T1D) is a form of diabetes mellitus that results from the autoimmune destruction of the insulin-producing beta cells in the pancreas. The resulting lack of insulin leads to increased blood and urine glucose.

Since Himsworth observations reported in 1936 (1), diabetes is usually considered to consist of two distinct diseases, namely, insulin-dependent type-1 diabetes (IDDM, T1D) driven by autoimmune beta-cell failure, and non-insulin-dependent type-2 diabetes (NIDDM, T2D) driven by peripheral resistance to insulin. This distinction in etiologies implies distinct treatment strategies, namely, insulin replacement for the treatment of T1D, as contrasted with insulin sensitizers (e.g., metformin, glitazones) and/or insulin secretagogues (e.g., sulphonylurea) and/or incretins (e.g., GLP1 analogues, DPP4 inhibitors) and/or insulin(s) for the treatment of T2D.

However, recent studies do indicate that the two diabetes diseases may overlap, namely, that systemic insulin resistance may promote T1D and that T2D may present islet-related antibodies.

For example, the CACTI study (2) and others point to systemic insulin resistance in well-controlled T1D patients (mean HbA1C 7.5%±0.9%), in terms of total body glucose turnover, hepatic glucose production and suppression of adipose lipolysis, as verified by hyperinsulinemic-euglycemic clamp.

In analogy to human T1D, insulin resistance has consistently been reported in animal models for autoimmune T1D (3, 4). Most importantly, systemic insulin resistance has recently been verified as risk factor for the progression of T1D (5), and to precede the overt diabetic stage in NOD mice (6, 8), implying that systemic insulin resistance may act as primary pathogenic driver in unmasking genetic predisposition to autoimmune beta-cell failure.

The apparent overlap in T1D and T2D etiologic drivers is also reflected in the course of T2D, where the insulin-resistant phenotype of T2D patients promotes beta-cell antigenicity, islet-related autoantibodies and cellular immune response (7). These considerations may imply that the two apparently distinct diabetes diseases may partially converge onto similar etiological targets/drivers (8, 9).

However, previous attempts to modify the disease course of T1D in animal models or patients by insulin sensitizers (e.g., metformin, thiazolidinediones (TZD)) have largely failed. Thus, use of metformin (10), or TZD (11), in the streptozotocin (STZ) diabetic rat model was reported to be ineffective or only marginally effective in normalizing STZ-induced diabetes, or in preventing or delaying autoimmune T1D in the NOD mouse model.

Similarly, use of metformin in insulin-treated (>1 u/kg body weight/day) T1D patients has recently been meta-analyzed and reported to result in negligible reduction in daily insulin usage (1.4 u/d) (12). Also, use of TZD in T1D patients was reported to be ineffective or counter effective in improving disease course (3, 14).

MEDICA analogues (15) consist of long-chain, α,ω-dioic acids (HOOC—C(α)—C(β)-Q-C(β')—C(α')—COOH, where Q represents a long-chain core element), substituted in the αα' (Mαα), ββ' (Mββ), and/or other optional core chain carbons. MEDICA analogues may be thio-esterified to their respective CoA-thioesters, but these are not esterified into lipids, nor converted into ceramides, while the substitutions at the αα' or ββ' positions block their β-oxidation. As such, MEDICA analogues may mimic allosteric activities of free/non-esterified long-chain fatty acids (LCFA) or their CoA thioesters, while avoiding β-oxidation or esterification into lipids.

MEDICA analogues are mostly excreted in bile as respective glucuronides MEDICA analogues proved efficacy in a series of obese, dyslipidemic, non-insulin-dependent type-2 diabetic and atherosclerotic animal models. Specifically, treatment of T2D animal models (e.g., db/db, ob/ob, fa/fa, cp/cp, Psamomys Obesus) with MEDICA analogues resulted in pronounced sensitization of liver, muscle and adipose tissue to insulin, decrease in plasma triglycerides and cholesterol levels, and suppression of agonist-induced adipose lipolysis (16-20).

It was previously reported that sensitization to insulin by MEDICA is driven by MEDICA-activated AMPK (10 to 20-fold higher efficacy than that of metformin (17), combined with suppression of STAT3 and the acute phase response (16).

Further information concerning MEDICA analogues and uses thereof can be found, for example, in WO 1986/000298 (21) and WO 1998/30350 (22).

General Description

The present disclosure provides a method of treatment of type 1 diabetes (T1D) in a subject in need thereof, wherein said subject is administered with standard of care doses of insulin or an insulin analogue, said method comprising administering to said subject a therapeutically effective amount of a compound of the general formula (I):

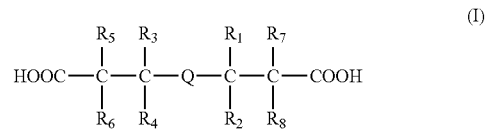

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

In some embodiments, administration of said compound of general formula (I) reduces the standard of care administered dose of insulin or insulin analogue. In other embodiments, administration of said compound of general formula (I) reduces the fasting blood glucose level and/or the HbA1c level in said subject.

The present disclosure further provides a method for reducing the standard of care administered dose of insulin or an insulin analogue, or for obviating the need for administration of insulin or an insulin analogue in a type 1 diabetic (T1D) subject in need thereof, said method comprising administering to said subject a therapeutically effective amount of a compound of the general formula (I):

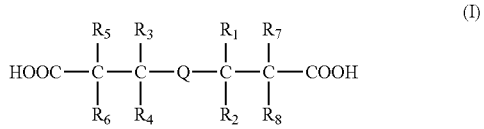

(I)

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

Still further the present disclosure provides a method of treating type 1 diabetes (T1D) in a subject diagnosed as having T1D by the presence of one or more autoantibody associated with T1D, wherein said subject is not administered with insulin or an insulin analogue, wherein said method comprises administering to said subject a therapeutically effective amount of a compound of the general formula (I):

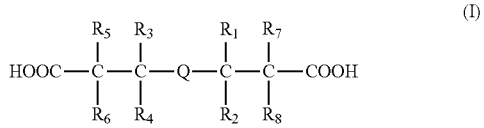

(I)

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;

wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

The present disclosure further provides a method of preventing or delaying the onset of insulin or an insulin analogue treatment in a T1D subject diagnosed as having T1D by the presence of one or more autoantibody associated with T1D, and wherein said subject is not administered with insulin or an insulin analogue, said method comprising administering to said subject a therapeutically effective amount of a compound of the general formula (I):

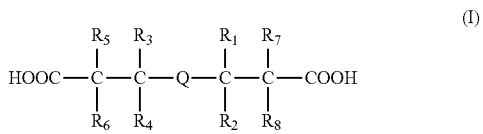

(I)

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

In some embodiments of the present disclosure the subject as herein defined was diagnosed as having blood glucose levels and/or HbA1c level below the standard of care threshold requiring administration of insulin or an insulin analogue.

In other embodiments of the present disclosure the at least one antibody associated with T1D is selected from the group consisting of islet cell autoantibodies, autoantibodies to insulin, autoantibodies to GAD, autoantibodies to tyrosine phosphatase and autoantibodies to the Zn transporter.

In the above and other embodiments the compound as herein defined is comprised in a pharmaceutical composition together with at least one pharmaceutically acceptable excipient or carrier.

In some embodiments the compound according to the present disclosure is administered at a therapeutically effective amount of about 5 mg to about 200 mg per subject per day, or of about 5 mg to about 100 mg per subject per day.

In other embodiments the compound according to the present disclosure is administered at a therapeutically effective amount of about 0.05 mg/kg to about 3.0 mg/kg per day.

In further embodiments the compound according to the present disclosure is administered once or twice daily, or once, twice or thrice weekly.

In some embodiments the compound as herein defined is administered orally. In other embodiments the compound as herein defined is administered in a unit dosage form, preferably capsule or tablet form.

In other embodiments in the compound of formula (I) as herein defined, Q represents a straight polymethylene chain $(CH_2)_n$, wherein n is an integer of from 6 to 14.

In some embodiments in the compound of formula (I) as herein defined, the hydrocarbyl is selected from the group consisting of an optionally substituted alkyl, alkenyl, alkynyl and cycloalkyl group, an optionally substituted aryl, and an optionally substituted aralkyl.

In further embodiments the alkyl as herein defined is a short-chain alkyl group of 1 to 4 carbon atoms, preferably a methyl group.

In some embodiments of the present disclosure the compound as herein defined is a compound of the formula (II):

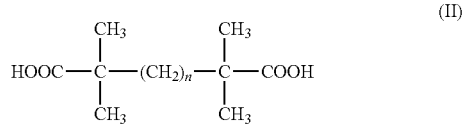

where n is an integer from 10 to 16, or a pharmaceutically acceptable salt, ester, amide, anhydride or lactone thereof.

In some embodiments the compound of formula (II) as herein defined is any one of 2,2,15,15-tetramethylhexadecane-1,16-dioic acid (referred to herein as M16αα), or 2,2,17,17-tetramethyloctadecane-1,18-dioic acid (referred to herein as M18αα) and 2,2,19,19-tetramethyleicosa-1,20-dioic acid (referred to herein as M20αα).

In specific embodiments the compound of formula (II) as herein defined is 2,2,15,15-tetramethylhexadecane-1,16-dioic acid (referred to herein as M16αα).

In other embodiments the compound according to the present disclosure is a compound of the formula (III):

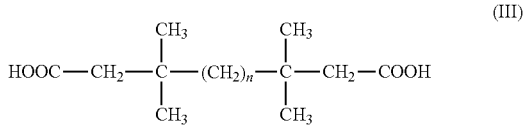

wherein n is an integer of from 8 to 14, or a pharmaceutically acceptable salt, ester, amide, anhydride or lactone thereof.

In specific embodiments the compound of formula (III) as herein defined is any one of 3,3,14,14-tetramethylhexadecane-1,16-dioic acid (referred to herein as M16ββ), or 3,3,16,16-tetramethyloctadecane-1,18-dioic acid (referred to herein as M18ββ) and 3,3,18,18-tetramethyleicosa-1,20-dioic acid (referred to herein as M20ββ).

In the above and other embodiments the salt as herein defined is a salt with an inorganic or organic cation, in particular alkali metal salt, alkaline earth metal salt, ammonium salt and substituted ammonium salt; said ester is a lower alkyl ester; said amide is a mono- and di-substituted; said anhydride is an anhydride with a lower alkanoic acid; and/or said lactone is formed by ring closure of either or both carboxylic groups with a free hydroxy substituent (or substituents) in the compound of formula (I).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A is a bar diagram showing FBG prior to (black) and following (grey) treatment of STZ or control (SHAM) rats with CMC or MEDICA16αα. Mean±SE (n=5-12 per group). *Significant as compared with respective basal FBG (P<0.05). #Significant as compared with respective SHAM/CMC rats (P<0.05). FIG. 1B is a diagram showing blood glucose level in an intraperitoneal glucose tolerance test (IPGTT). Mean±SE (n=8-13 per group). FIG. 1C is a bar diagram showing food/water consumption and urine secretion. Mean of 24 hours±SE (n=7-10 per group). *Significant as compared with STZ/CMC rats (P<0.05). FIG. 1D presents bar diagrams showing plasma and pancreas insulin and glucagon content. Mean±SE (n=5-12 per group). *Significant as compared with STZ/CMC rats (P<0.05). Abbreviations: FBG, fasting blood glucose; CMC, carboxymethyl cellulose; b.i.d., twice a day; STZ, streptozotocin; STZ/CMC, STZ diabetic rats treated with CMC; STZ/MEDICA NonR, STZ diabetic rats treated with MEDICA16αα, where treatment resulted in FBG >250 mg/dl; STZ/MEDICA Res, STZ diabetic rats treated with MEDICA16αα, where treatment resulted in FBG <250 mg/dL; SHAM/CMC, SHAM (control) rats treated with CMC; and SHAM/MEDICA, SHAM (control) rats treated with MEDICA16αα.

FIG. 2A is a bar diagram showing FBG prior to (black) and following (grey) treatment. Mean±SE (n=5-12 per group). Treatment of STZ diabetic animals with a combination of a sub-therapeutic dose of insulin NPH (3 u/kg bw i.p b.i.d) combined with oral add-on MEDICA ("STZ/MEDICA NPH"), resulted in normalizing FBG in all STZ diabetic animals. *Significant as compared with respective basal FBG (P<0.05). #Significant as compared with respective SHAM/CMC rats (P<0.05). FIG. 2B is a diagram showing blood glucose level in IPGTT. Mean±SE (n=7 per group). Inset (upper bar graph) shows area under the curve (AUC) of blood glucose during IPGTT. Mean±SE. *Significant as compared with STZ/NPH rats (P<0.05). #Significant as compared with STZ/CMC rats (P<0.05). FIG. 2C is a graph showing blood glucose level in an intraperitoneal insulin tolerance test (IPITT) (% change of blood glucose). Mean±SE (n=8-10 per group). Inset-Initial slope of blood glucose curve during IPITT. *Significant as compared with STZ/NPH rats (P<0.05). #Significant as compared with STZ/CMC rats (P<0.05). FIG. 2D is a bar graph showing food/water consumption and urine secretion. Mean of 24 hours±SE (n=7-10 per group). *Significant as compared with STZ/NPH rats (P<0.05). Abbreviations: as in FIG. 1; NPH Neutral Protamine Hagedorn.

FIG. 3A presents bar diagrams showing the level of hepatic G6Pase and PEPCK transcripts. FIG. 3B is a bar diagram showing the level of hepatic phospho-CREB(Ser179). FIG. 3C is a bar diagram showing the level of hepatic cyclic AMP (cAMP). FIG. 3D is a bar diagram showing the level of hepatic phospho-CRTC2(Ser171). FIG. 3E is a bar diagram showing the level of hepatic phospho-ACC(Ser79). Abbreviations: ACC, Acetyl-CoA carboxylase; cAMP, cyclic AMP; CREB, cAMP response element binding protein; CRTC2, CREB-regulated transcription coactivator 2; G6Pase, Glucose-6-phosphatase; PEPCK, phosphoenol pyruvate carboxykinase.

FIG. 4A is a bar diagram showing soleus cellular GLUT4 content. Inset shows representative blots. FIG. 4B is a bar diagram showing soleus sarcolemma GLUT4 content. Mean±SE (n=3 per group. 81 fields per rat). Inset shows representative micrographs. FIG. 4C is a bar diagram showing soleus phospho-AS160(Thr642). FIG. 4D is a bar diagram showing soleus phospho-ACC(Ser79). FIG. 4E is a bar diagram showing soleus phospho-Akt(Ser473).

FIGS. 5A-5B. Prevention of overt type 1 diabetes (T1D) by MEDICA16αα in Non-obese diabetic (NOD) mice. NOD mice were non-treated (squares) (n=28) or treated by MEDICA16αα(diamonds) in feed (40 mg MEDICA16αα/kg body weight per day) (n=24) from weaning (3 weeks) on. FIG. 5A is a Kaplan Meier curve presenting the percentage of MEDICA16αα-treated and non-treated NOD mice that remained non-diabetic within the indicated time period. FIG. 5B presents graphs showing body weight, daily food consumption, and daily food consumption per body weight gain within the indicated time period.

FIG. 6A presents islet insulitis scores of MEDICA16αα-treated and non-treated 14-week old NOD mice (n=10 per group). Inset shows representative insulitis scores. FIG. 6B is a graph showing blood glucose level during IPGTT in MEDICA16αα-treated (diamond) and non-treated (square) 14-week old NOD mice. The inset shows area under the blood glucose curve (AUC) during IPGTT and glucose-stimulated plasma insulin during the first 30 min of IPGTT. Mean±SE (n=12-18 per group). *Significant as compared to non-treated mice (P<0.05). FIG. 6C is a graph showing blood glucose level during IPGTT in MEDICA16αα-treated (diamond) and non-treated (square) 25-week old NOD mice. The inset shows area under the blood glucose curve (AUC) during IPGTT and glucose-stimulated increase in plasma insulin during the first 30 min of IPGTT. Mean±SE (n=6-8 per group). *Significant as compared to non-treated mice (P<0.05).

FIG. 7A is a time course measurement of blood glucose level (0-120 min). FIG. 7B is a bar diagram showing basal and clamped (80-120 min) blood insulin. FIG. 7C upper frame is a graph showing a time course of glucose infusion rate (GIR) and lower frame is a graph showing a GIR-AUC0-120 (area under the glucose infusion curve) and a graph showing a GIR-AUC80-120/Insulin (area under the glucose infusion curve during the 80-120 min period, relative to concomitant clamped plasma insulin). FIG. 7D upper frame is a bar diagram showing basal and clamped levels of endogenous glucose production and lower frame is a bar diagram showing the percentage suppression of endogenous glucose production relative to concomitant clamped plasma insulin. FIG. 7E is a bar diagram showing the basal and clamped glucose turnover relative to concomitant plasma insulin. FIG. 7F upper frame is a bar diagram showing Soleus and Gastrocnemius insulin-stimulated glucose utilization (Rg) and lower frame is a bar diagram showing Soleus and Gastrocnemius Rg relative to concomitant clamped plasma insulin.

DETAILED DESCRIPTION OF EMBODIMENTS

The present disclosure is based on the surprising finding that systemic sensitization to insulin by the compound HOOC—C(CH$_3$)$_2$—(CH$_2$)$_{12}$—C(CH$_3$)$_2$—COOH, also designated herein "MEDICA16αα", "Medica16αα" or M16αα, ameliorated the course of the disease in an overt type 1 diabetes (T1D) animal model, to a certain extent even in the absence of administration of insulin, and prevented or delayed the development of autoimmune pre-T1D into overt T1D.

The effect of MEDICA16αα in the context of T1D was first studied in a rat model of type 1 diabetes. As shown in FIG. 1 and as detailed in the Examples below, oral administration of MEDICA16αα resulted in an all-or-none response, whereby the fasting blood glucose (FBG) was normalized in about 40% of MEDICA16αα-treated diabetic rats (FIG. 1A), being further accompanied by essentially normalized glucose tolerance test (FIG. 1B).

Figure 1A:
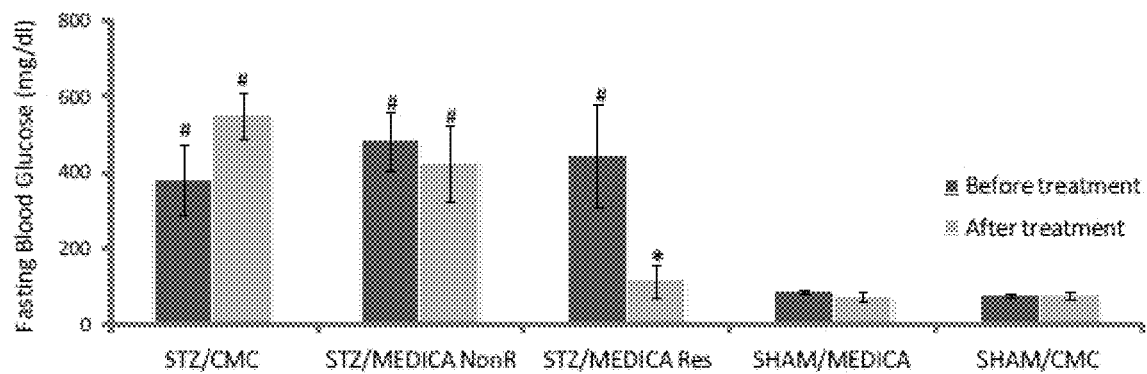
FIGS. 1A-1D. Anti-diabetic efficacy of MEDICA16αα in streptozotocin (STZ) diabetic rats. Streptozotocin (STZ) diabetic rats (having a fasting blood glucose (FBG) >300 mg/dl) or control (SHAM) rats were treated for 10 consecutive days with oral 2,2,15,15-tetramethylhexadecane-1,16-dioic acid, also referred to herein as MEDICA16αα or M16αα (15 mg/kg twice a day (b.i.d)) or with carboxymethyl cellulose (CMC) vehicle as indicated. M16αα treatment resulted in all-or-none response, whereby the FBG was normalized in about 40% of STZ diabetic rats ("STZ/MEDICA Responsive (Res)"), while 60% of the M16αα-treated rats remained nonresponsive ("STZ/MEDICA Non-Responsive (NonR)").
Figure 1B:
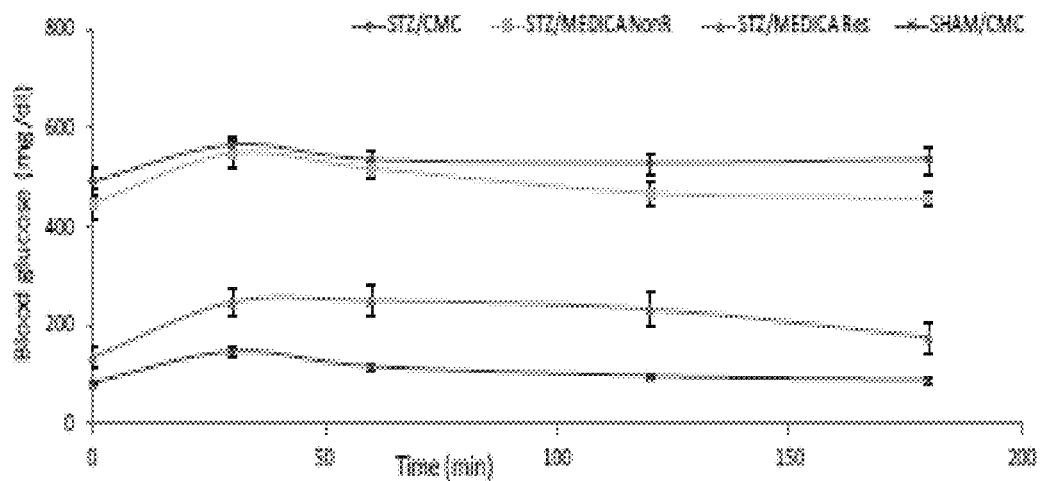

Remarkably, however, 60% of the MEDICA16αα-treated diabetic rats were non-responsive to treatment with the compound, based on their FBG and glucose tolerance (FIGS. 1A, B). Thus, the effect of administering a combination of MEDICA16αα and sub-therapeutic dose of insulin was then examined in this overt diabetic animal model. Surprisingly, the combined treatment was shown inter alia, to normalize FBG (FIG. 2A), glucose tolerance (IPGTT) (FIG. 2B), insulin tolerance (IPITT) (FIG. 2C) and fluid balance (FIG. 2D) in all (100%) diabetic animals that were non-responsive to MEDICA16αα stand-alone.

Of note, the concerned sub-therapeutic dose of insulin NPH was without any effect in controlling glycemia, IPGTT, IPITT or fluid balance in STZ diabetic rats in the absence of add-on MEDICA16αα(FIG. 2), implying a requirement for the combined MEDICA16αα/insulin treatment.

Therefore, by one of its aspects the present disclosure provides a method of treatment of type 1 diabetes (T1D) in a subject in need thereof, wherein said subject is administered with standard of care doses of insulin or an insulin analogue, said method comprising administering to said subject a therapeutically effective amount of a compound of the general formula (I):

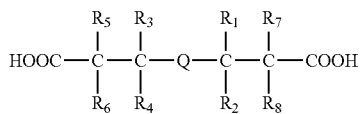

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

As known in the art, "type 1 diabetes" (T1D), also known as "Insulin-dependent type-1 diabetes" (IDDM) or "Diabetes mellitus type 1" (formerly insulin-dependent diabetes or juvenile diabetes) is a form of diabetes mellitus that results from autoimmune destruction of the insulin-producing beta cells in the pancreas, which is manifested by increased blood and urine glucose. Autoimmune markers include islet cells autoantibodies, autoantibodies to insulin, autoantibodies to glutamate decarboxylase (GAD65), autoantibodies to tyrosine phosphatase 1A2 and 1A2b, and autoantibodies to Zn transporter 8 (ZnT8). Symptoms of T1D include polyuria (frequent urination), polydipsia (increased thirst), polyphagia (increased hunger) and weight loss.

The rate of autoimmune beta-cell destruction is quite variable, being rapid in some individuals (mainly children) and slow in others (mainly adults). Children and adolescents may present with ketoacidosis as a first manifestation of the disease. Others present with hyperglycemia with or without ketoacidosis. Adults may retain sufficient beta-cell function to prevent ketoacidosis for many years. At the later stage of the disease there is little or no insulin secretion, as manifested by low or undetectable plasma c-peptide.

Criteria for insulin treatment of T1D patients according to the American Diabetes Association (ADA) include the following: a fasting plasma glucose (FPG) level ≥126 mg/dL (7.0 mmol/L), and/or a 2-hour plasma glucose level ≥200 mg/dL (11.1 mmol/L) during a 75-g oral glucose tolerance test (OGTT), and/or random plasma glucose ≥200 mg/dL (11.1 mmol/L).

Administration of insulin to subjects diagnosed as having T1D is essential for survival. Insulin therapy must be continued indefinitely. People are usually trained to independently manage their diabetes; however, for some this can be challenging. Untreated diabetes can cause many complications. Acute complications include diabetic ketoacidosis and nonketotic hyperosmolar coma. Serious long-term complications include heart disease, stroke, kidney failure, foot ulcers and damage to the eyes. Furthermore, complications may also arise from low blood sugar, weight gain, fatty liver and neurodegeneration caused by excessive insulin treatment.

Control of T1D is performed by routine measuring FBG or by measuring random plasma glucose level. An additional parameter for assessment of T1D status is the HbA1c level.

The term "HbA1c" (also termed haemoglobin A1c or A1c) as known in the art refers to glycated haemoglobin. By measuring glycated haemoglobin (HbA1c), clinicians obtain an overall picture of what the average blood sugar levels have been over a period of weeks/months (about 120 days). According to standard of care practice, a level of HbA1c is said to be "normal" (and is not indicative of a disease state) when below 5.7%. A level of HbA1c which indicates prediabetes is in the range of 5.7% to 6.4% and a level of HbA1c which indicates diabetes is 6.5% or over. The higher the HbA1c, the greater the risk of developing diabetes-related complications.

As detailed above, administration of insulin is essential for T1D patient's survival. Therefore, standard of care treatment of T1D includes administration of insulin or an insulin analogue to a T1D patient.

The term "Insulin" as known in the art refers to a peptide hormone which is produced endogenously by beta cells in the pancreas. Insulin regulates the metabolism of carbohydrates and fats by promoting the absorption of glucose from the blood to skeletal muscles and fat tissue and by causing fat to be stored rather than used for energy. Insulin also inhibits the production of glucose by the liver.

The present disclosure contemplates use of any type of insulin or insulin analogue in combination with the compound of formula (I) as herein defined. Non limiting examples of insulin types are rapid-acting, regular or short-acting, intermediate-acting and long-acting insulin, as known in the art and as defined below.

The term "rapid-acting insulin" refers to an insulin that begins to work about 15 minutes after injection, peaks in about 1 hour, and continues to work for 2 to 4 hours (for example insulin glulisine (Apidra), insulin lispro (Humalog), and insulin aspart (NovoLog)).

The term "regular or short-acting insulin" refers to an insulin that usually reaches the bloodstream within 30 minutes after injection, peaks anywhere from 2 to 3 hours after injection, and is effective for approximately 3 to 6 hours (for example Humulin R, Novolin R).

The term "intermediate-acting insulin" refers to an insulin that generally reaches the bloodstream about 2 to 4 hours after injection, peaks 4 to 12 hours later, and is effective for about 12 to 18 hours (for example NPH (Humulin N, Novolin N)).

The term "long-acting insulin" or "basal insulin" refers to insulin that reaches the bloodstream several hours after injection and tends to lower glucose levels fairly evenly over a 24-hour period (for example insulin detemir (Levemir) and insulin glargine (Lantos)).

The term "insulin analogue" as known in the art and as herein defined refers to an altered form of insulin, which differs from naturally occurring insulin, but is able to perform the same biological activity as naturally occurring human insulin in terms of glycemic control.

Examples of insulin analogues encompassed by the present disclosure include, but are not limited to, insulin molecules that are more readily absorbed from the injection site and therefore act faster than natural insulin injected subcutaneously, intended to supply the bolus level of insulin needed at mealtime (rapid-acting insulin, e.g. prandial insulin, insulin glulisine, insulin lispro and insulin aspart) and/or insulin molecules that are released slowly over a period of between 8 and 24 hours, intended to supply the basal level of insulin during the day and particularly at nighttime (intermediate- and long-acting insulin, e.g. Insulin detemir and insulin glargine).

As indicated above, the present disclosure provides a method of treatment of type 1 diabetes (T1D) in a subject in need thereof, wherein said subject is administered with standard of care doses of insulin or an insulin analogue, said method comprising administering to said subject a therapeutically effective amount of a compound of the general formula (I).

The term "standard of care administered dose of insulin or an insulin analogue" as known in the art and as herein defined refers to doses of insulin (or an insulin analogue) required for maintaining glycemic control. Standard of care doses of insulin or an insulin analogue can be determined by a skilled physician trained in the field of the invention. A non-limiting example of a standard of care dose of insulin is 1 u insulin/kg body weight/day (1 unit insulin per kg of body weight per day).

The standard of care doses of insulin or an insulin analogue for maintaining glycemic control in T1D patients is determined on a case by case basis and relies on various parameters. For example, high glucose threshold is recommended for patients with hypoglycemia unawareness.

Currently, doses of insulin or an insulin analogue for maintaining glycemic control in T1D patients are determined, at least in part, by T1D patients themselves, based on self-measurement of blood glucose level (using a portable glucose monitoring system, or insulin pump), and according to their needs, for example matching prandial insulin to carbohydrate intake, pre-meal blood glucose, or anticipated physical activity.

As known in the art an "insulin pump" refers to a small computerized device that can be programmed to release small doses of insulin continuously (basal), or a bolus dose close to mealtime to control the rise in blood glucose after a meal. This delivery system most closely mimics the body's normal release of insulin.

In specific embodiments the present disclosure provides a method of treatment of type 1 diabetes (T1D) in a subject in need thereof, wherein said subject is administered with standard of care doses of insulin or an insulin analogue, said method comprising administering to said subject a therapeutically effective amount of a compound of the general formula (I), where the compound is 2,2,15,15-tetramethyl-hexadecane-1,16-dioic acid (referred to herein as MEDICA16αα or M16αα, as detailed above).

As detailed above, MEDICA16αα as an add-on to (or in combination with) sub-therapeutic insulin doses resulted in normalizing fasting blood glucose, as well as glucose and insulin tolerance. As detailed herein below, MEDICA16αα efficacy in ameliorating streptozotocin (STZ)-induced diabetes was not accounted for by increasing pancreatic or plasma insulin, or by suppressing glucagon.

Without wishing to be bound by theory, MEDICA16αα efficacy may be ascribed to systemic sensitization to insulin, resulting in amplifying and potentiating sub-therapeutic insulin into an effective therapeutic measure, while reducing the standard of care doses of insulin (or insulin analog) used for treating type 1 diabetic patients. Surprisingly, the higher performance of MEDICA16αα in the STZ animal model shown below as compared to metformin (10) may be partially ascribed to its potent AMPK activation, surpassing that of metformin by about 10 to 20-fold (16, 17).

Most importantly, as shown in the Examples below, treating STZ diabetic animals with a combination of a sub-therapeutic dose of Neutral Protamine Hagedorn NPH insulin (at only 3 u/kg body weight, i.p, twice per day) with oral MEDICA16αα resulted in normalizing FBG in all (100%) STZ diabetic animals. Of note, the above sub-therapeutic dose of insulin NPH per se was without any effect in controlling glycemia, IPGTT, IPITT or fluid balance in STZ diabetic rats.

Thus, sensitization to insulin may result in decreasing the injected insulin doses required to maintain glycemic control in a T1D patient. Decreasing the injected insulin doses may avoid the pleiotropic adverse effects of insulin in promoting the macro vascular disease of T1D, in increasing body-weight gain, in increasing the fat content of liver, skeletal and heart muscles, and in increasing cancer (pancreatic, colorectal, breast, other) risk (23, 24). Since T1D patients are treated by insulin injected systemically, the concerned systemic insulin exposure may result in adverse effects beyond those exerted by endogenous beta-cell insulin, whereby 50% of which is cleared by first-pass in the liver.

Therefore, in some embodiments the administration of said compound of general formula (I) reduces the standard of care administered dose of insulin or insulin analogue.

By the term "reduces" it is hereby referred to any reduction, restriction, or decrease of the administered dose of insulin or insulin analogue, by at least about 1%-100%, about 5%-95%, about 10%-90%, about 15%-85%, about 20%-80%, about 25%-75%, about 30%-70%, about 35%-65%, about 40%-60% or about 45%-55%. Said reduction, restriction, or decrease of the administered dose of insulin or insulin analogue may also be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

In some embodiments the reduction, restriction, or decrease of the administered dose of insulin or insulin analogue may be by about 100%, namely obviating the need for administering exogenous insulin or insulin analogue to a T1D patient.

In some embodiments administration of the compound of general formula (I) according to the present disclosure reduces the fasting blood glucose level and/or the HbA1c level in said subject.

By the term "reduces the fasting blood glucose level and/or the HbA1c level in said subject" it is meant reducing, decreasing or lowering the fasting blood glucose level and/or the HbA1c level in said subject by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% such that in said T1D patient the fasting plasma glucose (FPG) level ≤126 mg/Dl (namely, lower than 126 mg/Dl) and the HbA1c level is below 7.0%.

By another aspect of the present disclosure there is provided a method for reducing the standard of care administered dose of insulin or an insulin analogue, or for obviating the need for administration of insulin or an insulin analogue in a type 1 diabetic (T1D) subject in need thereof, said method comprising administering to said subject a therapeutically effective amount of a compound of the general formula (I):

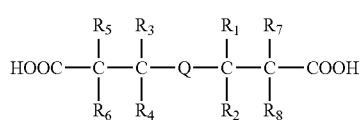

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

In specific embodiments the compound of formula (I) is 2,2,15,15-tetramethylhexadecane-1,16-dioic acid (referred to herein as M16αα).

As detailed herein, MEDICA16αα and insulin (or insulin analogue) are administered as a combination therapy. The term "combination therapy" as used herein refers to concurrent or consecutive administration of the two agents (namely the compound of formula (I) and the insulin or the insulin analogue). For example, concurrent administration can mean one dosage form in which the two or more agents are contained whereas consecutive administration can mean separate dosage forms administered to the patient at different times and by different routes of administration.

As indicated above, in about 40% of the MEDICA16αα-treated diabetic rats the fasting blood glucose (FBG) was normalized and the blood glucose level was ameliorated as demonstrated by a glucose tolerance test (this effect was also demonstrated in NOD mice). Remarkably, these diabetic rats were treated by MEDICA16αα stand-alone, namely, they were not administered with insulin.

By the term "subject in need thereof" or "patient" as used herein it is generally meant any organism who may be affected by any one of T1D (as described above) and T1D prediabetes (detailed below), and to whom the treatment methods herein described are desired, including humans diagnosed as having type 1 diabetes (T1D), whether treated just by diet and exercise, or with insulin or an insulin analogue. The term "subject in need thereof" also refers to other animals.

The present disclosure also encompasses subjects diagnosed as T1D prediabetic or T1D honeymoon. The term "T1D prediabetes" or "T1D honeymoon" (also referred to as "borderline diabetes") as known in the art is characterized by the presence of one or more autoantibodies associated with T1D, and blood glucose levels or HbA1c levels that are higher than normal but are not high enough according to standard of care recommendations to require administration of insulin or an insulin analogue, as detailed for example in the criteria for insulin treatment of T1D patients above.

The term "autoantibodies associated with T1D" as herein defined refers to any autoantibody that the presence of which in the blood of a subject indicates the risk of developing T1D. Several islet cell-specific autoantigens have been identified, for example (but not limited to) glutamic acid decarboxylase 65 (GAD65), the tyrosine phosphatase-related islet antigen 2 (IA-2), and insulin. Therefore, autoantibodies associated with T1D are for example islet cells autoantibodies, autoantibodies to insulin, autoantibodies to glutamate decarboxylase (GAD65), autoantibodies to tyrosine phosphatase 1A2 and 1A2b, and autoantibodies to Zn transporter 8 (ZnT8).

Autoantibodies directed against these autoantigens and other autoantibodies associated with T1D may be specifically detected in relatives of T1D probands before the clinical onset of diabetes, and detection of one or more islet autoantibodies is an early marker of progression to T1D.

Subjects diagnosed as having a level of one or more autoantibodies associated with T1D above a predetermined threshold are not administered with insulin (or an insulin analogue) as long as their endogenous insulin level is sufficient for maintaining a fasting blood glucose (FBG) level below 130 mg/dL before meals, or below 150 mg/dL at bedtime (or overnight), or Hemoglobin A1c (HbA1c) value below 7.5%.

Therefore, the present disclosure further provides a method of treating type 1 diabetes (T1D) in a subject diagnosed as having T1D by the presence of one or more autoantibodies associated with T1D, wherein said subject is not administered with insulin or an insulin analogue, wherein said method comprises administering to said subject a therapeutically effective amount of a compound of the general formula (I):

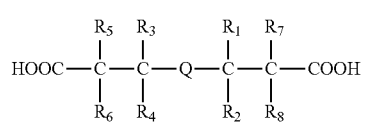

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

In some embodiments the at least one antibody associated with T1D is selected from the group consisting of islet cell autoantibodies, autoantibodies to insulin, autoantibodies to GAD, autoantibodies to tyrosine phosphatase and autoantibodies to the Zn transporter.

Figure 5A:
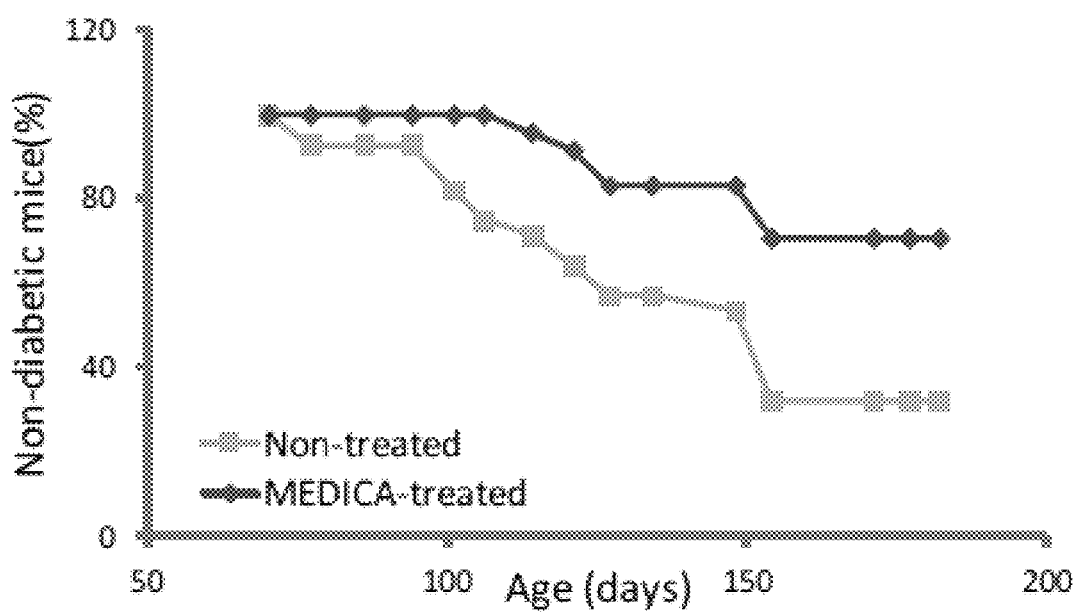
Figure 6A:
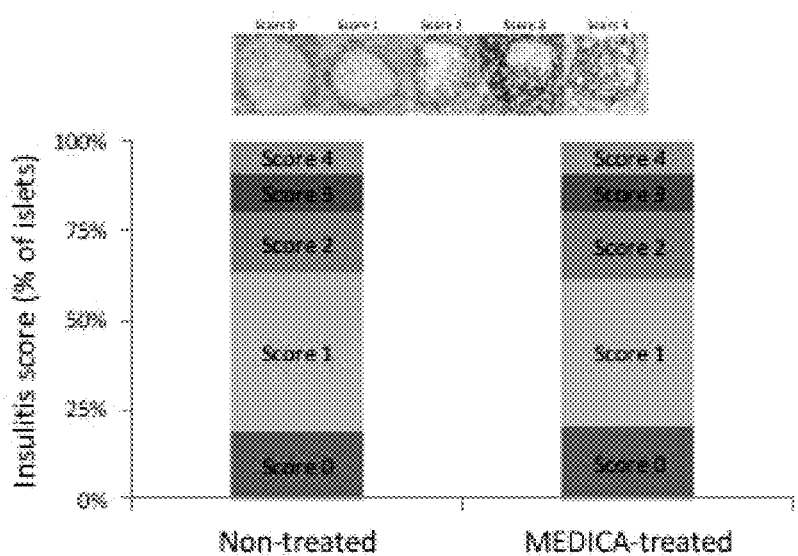
FIGS. 6A-6C. Islet insulitis scoring in MEDICA16αα-treated NOD mice. NOD mice were treated under the conditions described in FIG. 5.
Figure 6B:
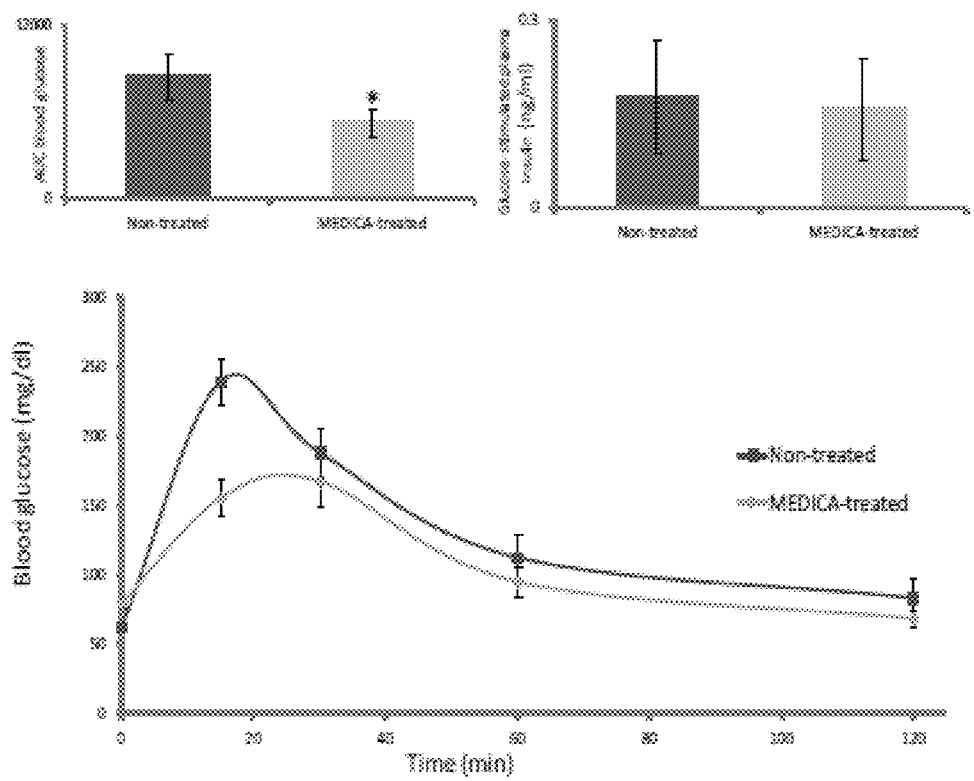
Figure 6C:
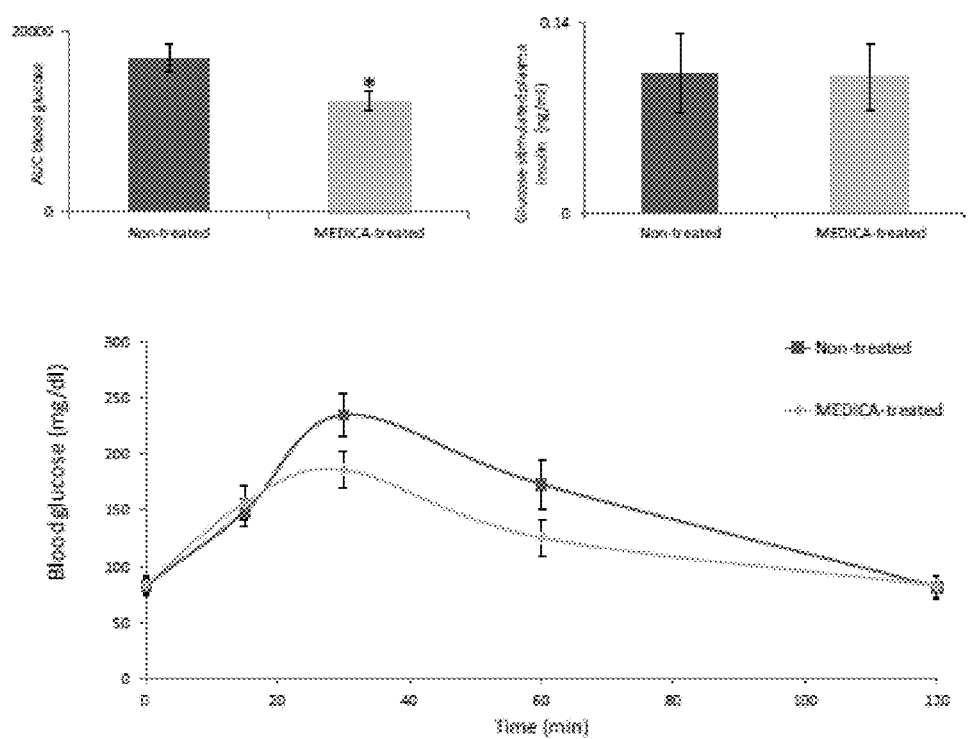

MEDICA16αα was shown to prevent or delay the development of autoimmune T1D in NOD mice, as evident from the results shown in FIG. 5A. As detailed below, MEDICA16αα treatment of NOD mice from weaning on until week 26 resulted in preventing T1D in 71% of mice as compared with 32% of non-treated animals. Here again, MEDICA16αα efficacy was not accounted for by improving the islet insulitis score of NOD mice, nor by improving insulin secretion in response to glucose load (FIG. 6). In contrast, and without being bound by theory, MEDICA16αα efficacy in preventing or delaying autoimmune T1D may be ascribed to systemic sensitization to insulin, resulting in suppressing hepatic glucose production, while increasing total body and muscle glucose uptake and turnover, as verified by euglycemic hyperinsulinemic clamp studies described below (FIG. 7).

Systemic insulin resistance has recently been verified in the pre-diabetic stage of NOD mice (3, 6), namely, in the absence of apparent glucolipotoxicity due to uncontrolled T1D, and prior to insulin treatment that could result in down-regulation of insulin receptors. The present disclosure further underscores the role played by insulin resistance in promoting autoimmune T1D due to an increase in beta-cell workload, and implies that systemic sensitization to insulin may counteract genetic predisposition to autoimmune beta cell failure and is therefore beneficial to subjects diagnosed as T1D prediabetic.

In other words, MEDICA16αα may counteract genetic predisposition to autoimmune T1D and amplify and potentiate sub-therapeutic insulin into an effective therapeutic measure. Treatment of T1D prediabetic patients with MEDICA16αα may extend T1D honeymoon and decrease insulin doses required for maintaining glycemic control of overt T1D.

Systemic sensitization to insulin may allow for beta-cell rest due to a decrease in beta-cell workload, resulting inter alia in a decrease in beta-cell antigenicity (25). As T1D patients may still retain residual beta-cells together with residual glucose-stimulated c-peptide secretion long after being treated with insulin or insulin analogue (26, 27), chronic T1D patients may still benefit from beta-cell rest driven by sensitization to insulin.

Therefore, by another one of its aspects the present disclosure provides a method of preventing or delaying the onset of insulin or an insulin analogue treatment in T1D subject diagnosed as having T1D by the presence of one or more autoantibody associated with T1D, and wherein said subject is not administered with insulin or an insulin analogue, said method comprising administering to said subject a therapeutically effective amount of a compound of the general formula (I):

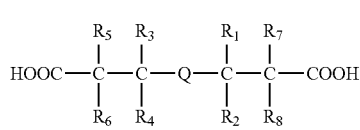

(I)

or a pharmaceutically acceptable salt, ester, amide, anhydride or lactone thereof, wherein (a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

A subject may be diagnosed as having one or more, for example one, two, three, four or more autoantibodies associated with T1D while the blood glucose levels and/or HbA1c level of said subject are below the standard of care threshold requiring administration of insulin or an insulin analogue. In such cases said subject is not administered with insulin or an insulin analogue.

Therefore, in some embodiments the subject encompassed by the present disclosure is diagnosed as having one or more, for example one, two, three, four or more autoantibodies associated with T1D and blood glucose levels and/or HbA1c level below the standard of care threshold requiring administration of insulin or an insulin analogue.

The term "preventing or delaying the onset of insulin or an insulin analogue treatment" as used herein means to avoid, inhibit, preclude or at least limit or restrict the onset of insulin or an insulin analogue treatment.

As detailed above, the present disclosure provides a method of treatment of type 1 diabetes (T1D) in a subject in need thereof under various conditions as herein defined. The term "treatment" or forms thereof as herein defined means to prevent, alleviate or ameliorate the patient's disease or condition.

The present disclosure encompasses administering a compound of formula (I) at a therapeutically effective amount to a subject in need thereof, which, as the case may be, is defined as a T1D diabetic patient or a T1D prediabetic patient (namely diagnosed as having at least one autoantibody associated with T1D). The term "therapeutically effective amount" as known in the art and as used herein is intended to mean that amount of a compound of formula (I) (for example, but not limited to, Medica16αα) that will elicit the desired biological or medical response which in the present case is long-term glycemic control. The therapeutically effective amount of a compound of formula (I) may be determined by a skilled physician.

For example, therapeutically effective amount of a compound of formula (I) may be partly determined by using an animal model, such as the animal models presented in the Examples below. As known in the art, overt T1D may be simulated by STZ-induced beta-cell failure in rats, where plasma glucose may reach values of 600 mg/dL. This and other animal models may be used for determining the efficacy of the administered amount of the compound.

As shown in FIG. 1A, oral administration of MEDICA16αα at 15 mg/kg twice daily resulted in a beneficial therapeutic effect. However, as known in the art, the therapeutically effective amount cannot be solely based on animal models, for example due to the disparity in ADME (Absorption, Distribution, Metabolism, Excretion) characteristics between animal models and humans.

In some embodiments the compound of formula (I) according to the invention is administered at a therapeutically effective amount of about 5 mg to about 200 mg per subject per day.

In other embodiments the compound of formula (I) according to the invention is administered at a therapeutically effective amount of about 5 mg to about 100 mg per subject per day.

In further embodiments the compound of formula (I) according to the invention is administered at a therapeutically effective amount of about 0.05 mg/kg to about 3.0 mg/kg per day.

In some embodiments the compound of formula (I) according to the invention may be administered once or twice daily, or once, twice, trice weekly, four, five, six or seven times per week.

In other embodiments the compound of formula (I) according to the invention is administered once or twice daily, or once, twice or thrice weekly.

In still further embodiments the compound of formula (I) according to the invention is administered in a unit dosage form, preferably capsule or tablet form.

The compound of formula (I) according to the present disclosure or any pharmaceutical composition comprising thereof can be administered and dosed in accordance with good medical practice, systemically, for example by enteral (e.g. oral, rectal) administration, or other.

As detailed herein below, Medica16αα was administered orally. Therefore, in some embodiments the compound of formula (I) as herein defined is administered orally.

The proposed administration of a compound of formula (I) according to the present disclosure may lead to the oral use of a non-insulin agent, for the treatment of type 1 diabetic or T1D prediabetic patients. As detailed above, this treatment regimen may result in limiting the insulin doses in type 1 diabetic patients or delay the onset of insulin treatment in T1D prediabetic patients, thereby reducing the risk for diabetic macrovascular diseases and insulin-induced cancer.

As detailed below, the present disclosure is based on the surprising effect of the compound HOOC—C(CH$_3$)$_2$—(CH$_2$)$_{12}$—C(CH$_3$)$_2$—COOH, also termed herein "MEDICA16αα", "Medica16αα" or M16αα.

Therefore contemplated by the present disclosure are α,ω-dioic acid compounds of the general formula (I):

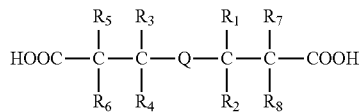

or a pharmaceutically acceptable salt, ester, amide, anhydride or lactone thereof, wherein
  (a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
  (b) each of $R_5$-$R_8$ is independently an unsubstituted or substituted hydrocarbyl and each of $R_1$-$R_4$ is hydrogen; wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

The term "hydrocarbyl" (molecules consisting entirely of hydrogen and carbon) in the definition of $R_1$-$R_8$ as herein defined and as known in the art includes, for example, optionally substituted alkyl (e.g. a $C_1$-$C_6$ alkyl), alkenyl (e.g. a $C_1$-$C_6$ alkenyl), alkynyl (e.g. a $C_1$-$C_6$ alkynyl), cycloalkyl, optionally substituted aryl, optionally substituted aralkyl and the like.

The term "substituted" in the context of the hydrocarbyl group as herein defined refers to a hydrocarbyl group in which one or more hydrogen atoms are independently replaced with the same or different substituent(s). Typical substituents include, but are not limited to halogen atoms, hydroxyl, lower alkoxy.

In some embodiments in said compound of formula (I), the hydrocarbyl is selected from the group consisting of an optionally substituted alkyl, alkenyl, alkynyl and cycloalkyl group, an optionally substituted aryl, and an optionally substituted aralkyl.

In other embodiments in said compound of formula (I), the alkyl is a short-chain alkyl group of 1 to 4 carbon atoms, preferably a methyl group.

The term "lower alkyl" and the term "lower alkoxy" refer respectively to an alkyl or alkoxy group of 1 to 6, specifically 1 to 4 carbon atoms.

As detailed above, in the compound having formula (I) Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

The term "diradical of a linear chain of 6 to 14 carbon atoms" as herein defined refers to a linear alkyl, alkenyl or alkynyl chain of 6 to 14 carbon atoms.

In some embodiments in said compound of formula (I), Q represents a straight polymethylene chain (CH$_2$)$_n$, wherein n is an integer of from 6 to 14.

As stated above, each of $R_1$-$R_4$ is independently an unsubstituted or substituted hydrocarbyl or each of $R_5$-$R_8$ is independently an unsubstituted or substituted hydrocarbyl. Where a specific molecule is substituted, such substitution may be, for example, by an atom or group selected from hydrogen, halide (I, Br, Cl, F), —CF$_3$, hydroxyl, amine (including primary, secondary, tertiary or quarternized amine) or nitro.

In further specific embodiments the compound according to the present disclosure is a compound of the formula (II):

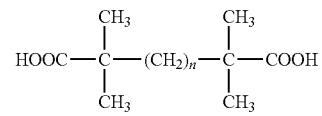

where n is an integer from 10 to 16, or a pharmaceutically acceptable salt, ester, amide, anhydride or lactone thereof.

In still further embodiments the compound of formula (II) is any one of 2,2,15,15-tetramethylhexadecane-1,16-dioic acid (referred to herein as M16αα), or 2,2,17,17-tetramethyloctadecane-1,18-dioic acid (referred to herein as M18αα) and 2,2,19,19-tetramethyleicosa-1,20-dioic acid (referred to herein as M20αα).

In the above and other embodiments, the compound of formula (II) is 2,2,15,15-tetramethylhexadecane-1,16-dioic acid (referred to herein as M16αα).

In other embodiments the compound according to the present disclosure is a compound of the formula (III):

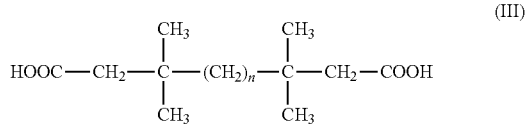

(III)

wherein n is an integer of from 8 to 14, or a pharmaceutically acceptable salt, ester, amide, anhydride or lactone thereof.

In some embodiments the compound of formula (III) is any one of 3,3,14,14-tetramethylhexadecane-1,16-dioic acid (referred to herein as M16ββ, or 3,3,16,16-tetramethyloctadecane-1,18-dioic acid (referred to herein as M18ββ) and 3,3,18,18-tetramethyleicosa-1,20-dioic acid (referred to herein as M20ββ).

Included within the scope of the present disclosure are derivatives of the α and/or ω carboxy groups of compounds of formula (I) which are capable of being hydrolyzed in vivo to yield the free diacids of formula (I), for example but not limited to a salt, ester, amide, anhydride or lactone of a compound of formula (I).

Thus the term "acceptable salt" as herein defined refers to salts with pharmaceutically acceptable inorganic or organic cations, in particular alkali metal salts, alkaline earth metal salts, ammonium salts and substituted ammonium salts. The term "acceptable esters" refers in particular to lower alkyl esters. The term "acceptable amides" refer to mono- and disubstituted amides and the term "acceptable anhydrides" refer for example to anhydrides with lower alkanoic acids. The term "acceptable lactones" as herein defined refers to lactones formed by ring closure of either or both carboxylic groups with a free hydroxy substituent (or substituents) in the molecule of formula (I).

In some embodiments the method according to the present disclosure is wherein said salt is a salt with an inorganic or organic cation, in particular alkali metal salt, alkaline earth metal salt, ammonium salt and substituted ammonium salt; said ester is a lower alkyl ester; said amide is a mono- and di-substituted; said anhydride is an anhydride with a lower alkanoic acid; and/or said lactone is formed by ring closure of either or both carboxylic groups with a free hydroxy substituent (or substituents) in the compound of Formula (I).

The presently disclosed subject matter relates to long-chain α,ω-dicarboxylic acid compounds of formula (I) and pharmaceutical compositions comprising same. The term "pharmaceutical compositions" as herein defined refers to the compound of formula (I) and optionally at least one pharmaceutically acceptable excipient or carrier as known in the art. As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions used to treat subjects in need thereof according to the present disclosure also comprise optionally a buffering agent, an agent who adjusts the osmolarity thereof, and optionally, one or more pharmaceutically acceptable additives as known in the art.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media.

It should be understood that in addition to the ingredients particularly mentioned above, the compositions as herein defined may also include other agents conventional in the art having regard to the type of formulation in question, for example those suitable for oral administration may include flavoring agents.

By another one of its aspects the present disclosure provides the use of the compound of formula (I) as herein defined, for the manufacture of a pharmaceutical composition for the treatment of type 1 diabetes (T1D) in a subject in need thereof, wherein said subject is administered with standard of care doses of insulin or an insulin analogue.

The present disclosure also encompasses use of the compound of formula (I) as herein defined for the manufacture of a pharmaceutical composition for reducing the standard of care administered dose of insulin or an insulin analogue, or for obviating the need for administration of insulin or an insulin analogue in a type 1 diabetic (T1D) subject in need thereof.

Still further the present disclosure provides use of the compound of formula (I) as herein defined for the manufacture of a pharmaceutical composition for the treatment of type 1 diabetes (T1D) in a subject diagnosed as having T1D by the presence of one or more autoantibody associated with T1D wherein said subject is not administered with insulin or an insulin analogue.

The present disclosure also encompasses use of the compound of formula (I) as herein defined for the manufacture of a pharmaceutical composition for preventing or delaying the onset of insulin or an insulin analogue treatment in a T1D subject diagnosed as having T1D by the presence of one or more autoantibody associated with T1D, wherein said subject is not administered with insulin or an insulin analogue.

By still another one of its aspects the present disclosure provides the compound of formula (I) as herein defined for use in a method of treatment of type 1 diabetes (T1D) in a subject in need thereof, wherein said subject is administered with standard of care doses of insulin or an insulin analogue.

The present disclosure also encompasses the compound of formula (I) as herein defined for use in a method of reducing the standard of care administered dose of insulin or an insulin analogue, or for obviating the need for administration of insulin or an insulin analogue in a type 1 diabetic (T1D) subject in need thereof.

Still further the present disclosure provides the compound of formula (I) as herein defined for use in a method of treating type 1 diabetes (T1D) in a subject diagnosed as having T1D by the presence of one or more autoantibody associated with T1D, wherein said subject is not administered with insulin or an insulin analogue.

The present disclosure also encompasses the compound of formula (I) as herein defined for use in a method of preventing or delaying the onset of insulin or an insulin analogue treatment in a T1D subject diagnosed as having T1D by the presence of one or more autoantibody associated with T1D, and wherein said subject is not administered with insulin or an insulin analogue.

In the above and other embodiments the compound of formula (I) is 2,2,15,15-tetramethylhexadecane-1,16-dioic acid (referred to herein as M16αα).

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

It must be noted that, as used in this specification and the appended claims, the singular forms "a", "an" and "the" include plural referents unless the content clearly dictates otherwise.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Animals

All animal procedures were approved by the Animal Experimentation Ethics Committee of the Hebrew University Hadassah Medical School in Jerusalem and adhered to the NIH Guide for the Care and Use of Laboratory Animals (NIH publication, 1996).

Streptozotocin (STZ) Diabetic Rats

Male Sprague-Dawley (SD) rats weighing 250-275 gr were fed ad libitum (Harlan Teklad 2018), had free access to water, and were kept on a 12:12 h light:dark cycle. Experimental type 1 diabetes (T1D) was induced in overnight fasted rats by a single intra-peritoneal injection of streptozotocin (STZ, 60 mg/kg body weight, Sigma Aldrich) freshly prepared in 0.1 M of cold citrate buffer (pH 4.5), followed by oral 10% glucose solution for the next 24 hours to overcome STZ-induced acute hypoglycemia. STZ diabetic rats (defined as having a fasting blood glucose (FBG) level higher than 300 mg/dl) were selected for further studies.

Treatment Protocol of STZ and SHAM Rats

SHAM (control) rats were injected with 0.1 M of cold citrate buffer (pH 4.5). STZ diabetic or SHAM rats were dosed twice daily by gavage (orally) with 1% CMC (Sigma Aldrich C5678), or with HOOC—C(CH$_3$)$_2$—(CH$_2$)$_{12}$—C(CH$_3$)$_2$—COOH (2,2,15,15-tetramethylhexadecane-1,16-dioic acid) also termed herein "MEDICA16αα", "Medica16αα" or M16αα(15 mg/kg body weight) suspended in 1% CMC, or injected intraperitoneal (i.p.) with Neutral Protamine Hagedorn (NPH) insulin (3 u/kg body weight b.i.d), as indicated.

Administering a combination of Medica16αα and insulin was performed by treating STZ diabetic rats (FBG >300 mg/dl) with oral MEDICA16αα(15 mg/kg b.i.d) for five consecutive days, then MEDICA16αα-responsive rats were further treated with MEDICA16αα(15 mg/kg b.i.d) for 10 additional consecutive days ("STZ/MEDICA Res"), and MEDICA16αα non-responsive rats (FBG >250 mg/dl) were further treated for 10 additional consecutive days with either insulin Neutral Protamine Hagedorn (NPH) (3 u/kg b.i.d subcutaneously) ("STZ/NPH"), or with insulin NPH (3 u/kg b.i.d subcutaneously in combination with oral MEDICA16αα(15 mg/kg b.i.d) ("STZ/MEDICA NPH").

Tail vein FBG was verified daily by a glucometer (Glucometer®, Accu-Check® Performa, Roche Diagnostics). Urine secretion, food and water consumption were measured in standard metabolic cages (Tecniplast™ Metabolic Cage Systems for Rodents) for 48 hour periods. Samples were collected and recorded every 12 hour.

Following treatment, rats were sacrificed, and blood and tissues were sampled for further studies.

Non-Obese Diabetic (NOD) Mice

NOD/LtJ mice (Harlan Laboratories) were bred in-house under pathogen-free conditions. Female mice (3-week old) were fed ad libitum from weaning on with standard chow (Harlan Teklad 2018), or with MEDICA16αα diet (0.04% (w/w) MEDICA16αα mixed in Teklad 2018, yielding a dose of 40 mg MEDICA16αα per kg body weight per day). Mice were monitored weekly for body weight and food consumption. Tail vein blood glucose was verified weekly from week 10$^{th}$ on, on a set day and hour. Mice were considered diabetic if presenting non-fasting blood glucose levels >300 mg/dl for 3 consecutive days. Diabetic mice were euthanized, and blood and tissues were sampled for further studies.

Intraperitoneal Glucose Tolerance Test (IPGTT)

Overnight fasted rats were injected i.p (1 gr glucose/kg bw) with 20% dextrose solution (Teva Medical). Tail vein blood was sampled on 0, 30, 60, 90 and 120 minutes following glucose injection.

Overnight fasted NOD mice were injected i.p (2 gr/kg bw) with standard 20% dextrose solution. Tail vein blood was sampled on 0, 15, 30, 60, 90 and 120 minutes. Blood glucose was measured by glucometer. Plasma insulin prior to and 30 min following glucose injection was measured using Ultrasensitive Mouse Insulin ELISA kit (Crystal Chem).

Intraperitoneal Insulin Tolerance Test (IPITT)

Fasted rats (5 hours fast) were injected i.p (2 u/kg bw) with HumulinR insulin (Eli Lilly). Tail blood glucose levels were measured by glucometer at 0, 15, 30, 60, and 120 min following insulin injection.

Euglycemic-Hyperinsulinemic Clamp

Clamps were carried out according to Vanderbilt Mouse Metabolic Phenotyping Center, Vanderbilt University School of Medicine protocol (28), with minor modifications, using HPLC-purified $^3$H-glucose (specific activity 13.5 Ci/mmol, MT-914 Moravek Biochemicals, priming dose of 1 µC followed by continuous infusion of 0.05 µCi·min-1 for a 90 min equilibration period), HumulinR insulin (Eli Lilly, 4 mU·kg-1. min-1), and 10% glucose solution.

Clamps were carried out in conscious 12-14-week old NOD female mice fasted for 3 hours, 3 days following catheters' insertion. Glucose, insulin and $^3$H-glucose steady state was reached at about 80 min following insulin infusion. Plasma glucose specific activity was verified on 80, 90, 100, and 120 min following insulin infusion. On 120 min, 12-µCi bolus of $^{14}$C-2-deoxyglucose (DG) (specific activity 274.6 mCi/mmol, MC-392 Moravek Biochemicals) was injected, followed by blood sampling on 122, 125, 130, 135, and 145 min, to determine blood glucose and 2-deoxyglucose activity.

Upon sacrifice, gastrocnemius, superficial vastus lateralis, and soleus muscles were removed, immediately frozen in liquid nitrogen, and stored at −70° C. until further analysis. Glucose appearance (Ra) and disappearance (Rd) were determined using Steele non-steady-state equations. Endogenous glucose production (EndoRt) was determined by subtracting the glucose infusion rate (GIR) from total glucose turnover (Rt). Glucose metabolic index in muscle (Rg) was calculated by the equation:

$$R_g = \frac{2[^{14}C]DGP_{tissue}}{AUC2[^{14}C]DG_{plasma}} \times [arterial\ glucose]$$

where $2[^{14}C]DGP_{tissue}$ is the $2[^{14}C]DG$ radioactivity in muscle normalized to tissue weight (dpm/g tissue), $AUC\ 2[^{14}C]DG_{plasma}$ is the area under the plasma $2[^{14}C]DG$ disappearance curve (dpm·min·m1-1), and [arterial glucose] is the average blood glucose (mmol/1) during the 80-120 min clamp period.

Immuno-Histochemistry

Muscle tissue was fixed with 4% buffered formaldehyde for 4 hours. Paraffin sections (5 µm) were rehydrated and antigen retrieved in citrate buffer using a Biocare pressure cooker, followed by 5 minutes blocking in peroxidase and 10 minutes of protein block (Cas-Block). The sample was incubated with anti-GLUT4 antibody (AbCam ab65267), followed by polyclonal anti-mouse IgG. DAB substrate buffer was then added to achieve coloration. The specimens were subsequently dehydrated with ethanol, cleared with xylene and then mounted on glass cover slips. Digital images were obtained using Nikon Eclipse TE-2000E microscope equipped with Olympus DP70 camera. Image analysis was carried out using ImageJ software.

Insulitis Score

Head of pancreas of NOD mice was sampled, fixed in 4% buffered formalin, embedded in paraffin, and 5-mm sections were stained with hematoxylin/eosin. Insulitis scores 0 to 4 were verified by the percentage of intra-islet mononuclear granulation ("0", no intra-islet mononuclear cell infiltration; "1", <25% of islet being infiltrated with mononuclear cell granulation; "2", 25%-50%; "3", 50-75%; "4", >75%), in 30 to 40 islets per pancreas.

Cell Lysis and Western Blotting

Sampled frozen tissue was homogenized (Polytron) in lysis buffer (50 mM Tris HCl, pH 8.0, 1% Triton X-100, 1 mM EGTA, 1 mM EDTA, 150 mM NaCl, 5 mM NaPPi, 50 mM NaF, 1 mM PMSF, 1 mM Na Vanadate, 40 nM bpVfan and protease inhibitor cocktail (Sigma)), and centrifuged for 15 min at 12,500 rpm.

Protein lysates were prepared in sodium dodecyl sulfate (SDS) sample buffer (62 mM Tris (pH 6.8), 2.3% SDS, 0.64 mM mercaptoethanol, 10% glycerol), and were subjected to SDS-PAGE, electro-transferred onto cellulose nitrate membranes (Schleicher & Schuell) and probed with the indicated first antibody, followed by HRP-labeled second antibody. Protein concentration was determined by BCA (Thermo Scientific). Bands were detected by ECL, and the intensity of individual bands was determined by densitometry using ImageJ 1.48 v software.

Immunoprecipitation

Sampled frozen tissue was homogenized (Polytron) in lysis buffer (50 mM Hepes (pH 7.4), 150 mM NaCl, 10% Glycerol, 1.5 mM MgCl2, 1 mM EGTA, 1% Triton, 50 mM β-glycerolphosphate, 25 mM NaF, 1 mM Na-vanadate, 40 nM bpVphen, protease inhibitor mix (Sigma) and 17.5 mg/ml octyl beta-D-glucopyranoside (Sigma)). Lysates were kept on ice for 30 min and centrifuged at 12000 rpm for 15 min. Lysates (250 m) were incubated for 4 h with protein A/G beads (Santa Cruz Biotechnology) pre-loaded with the indicated antibody. The immune-precipitate was rinsed 3 times with washing buffer (20 mM Hepes (pH 7.4), 150 mM NaCl, 0.1% Tx-100, 10% glycerol), re-suspended in SDS sample buffer, boiled for 8 min, and analyzed by SDS-PAGE.

RT-PCR

Total RNA was prepared using the TRI reagent (Sigma Aldrich). First-strand cDNA used as template was synthesized by reverse transcription using oligo(dT) as primer and the Reverse-iTMAX First Strand Kit (ABgene, Epson). Glucose-6-phosphatase (G6Pase) and phosphoenolpyruvate carboxykinase (PEPCK) transcripts normalized by tubulin were quantified by real-time PCR (Rotor Gene RG-3000A) using SYBER green MasterMix (Absolute Syber Green ROX Mix, ABgene) and the following primers:

```
G6Pase
                                       (SEQ ID NO: 1)
Forward primer:    5'-TCATCTTGGTGTCCGTGATCG-3';

(SEQ ID NO: 2)
Reverse primer:    5'-TTTATCAGGGGCACGGAAGTG-3';

PEPCK
                                       (SEQ ID NO: 3)
Forward primer:    5'-GGCCACAGCTGCTGCAG-3';

(SEQ ID NO: 4)
Reverse primer:    5'-GGTCGCATGGCAAAGGG-3';

Tubulin
                                       (SEQ ID NO: 5)
Forward primer:    5'-TAGCAGAGATCACCAATGCC-3';

(SEQ ID NO: 6)
Reverse primer:    5'-GGCAGCAAGCCATGTATTTA-3'.
```

Bioanalysis

Pancreas and plasma insulin and glucagon content were determined by insulin (Millipore, Cat #RI-13K) and glucagon (Millipore, Cat # GL-32K) radioimmunoassay (RIA) kits. cAMP levels were measured by cAMP kit (Arbor Assays, DetectX Cat # K019-H1).

MEDICA16αα Analysis

Plasma aliquots of 100 µl were vortex-mixed with 50 µl of formic acid:methanol (1:1 v/v) solution containing an internal standard, extracted into n-hexane, centrifuged, and the hexane layer was evaporated to dryness. The residue was reconstituted in the mobile phase and injected into the LC/MS system [Waters Micromass ZQ mass spectrometer (Waters Co.)]. LC/MS conditions were as follows:)(Bridge MS; RP8 column, 3.5 μm, 2.1×100 mm column (Waters Co.); column temperature was 35° C.; isocratic mobile phase, methanol:water (82:18 v/v) containing 0.1% formic acid, at a flow rate of 0.2 ml/min; detector tuned to 500 L/hr nitrogen flow; source temperature; 400° C.; cone voltage 30V; ionization mode ESI+; 365 and 393 m/z for MEDICA16αα and the internal standard, respectively. Calibration curves were linear and validated in the 100 ng/ml to 5000 ng/ml range, with accuracy of 7-9% relative error and precision of 8-10% relative standard deviation.

Statistics

Values are presented as Mean±SEM. Significant differences between groups ($P<0.05$) were verified by Student's t-test (2 groups) or analysis of variance (≥3 groups).

Example 1 Effect of MEDICA16αα in Streptozotocin (STZ) Diabetic Rats

The effect of the compound HOOC—C(CH$_3$)$_2$—(CH$_2$)$_{12}$—C(CH$_3$)$_2$—COOH, also termed herein "MEDICA16αα", "Medica16αα" or M16αα, in the context of T1D was first studied in a rat model of type 1 diabetes induced by streptozotocin (STZ). Streptozotocin is a naturally occurring chemical that is particularly toxic to the insulin-producing beta cells of the pancreas in mammals. As indicated above, the initial fasting blood glucose (FBG) of these STZ diabetic rats amounted to 350-450 mg/dL, reaching levels of 550 mg/dL in vehicle (carboxymethyl cellulose (CMC))-treated animals.

As shown in FIG. 1A, oral administration of MEDICA16αα at 15 mg/kg twice daily as described above resulted in an all-or-none response, whereby the FBG was normalized (FBG<250 mg/dL) in about 40% of the STZ diabetic MEDICA16αα-treated rats (this group is also termed herein "STZ/MEDICA Responsive (Res)").

However, 60% of the MEDICA16αα-treated STZ rats remained non responsive (this group is also termed herein "STZ/MEDICA NonResponsive (NonR)").

Figure 1C:
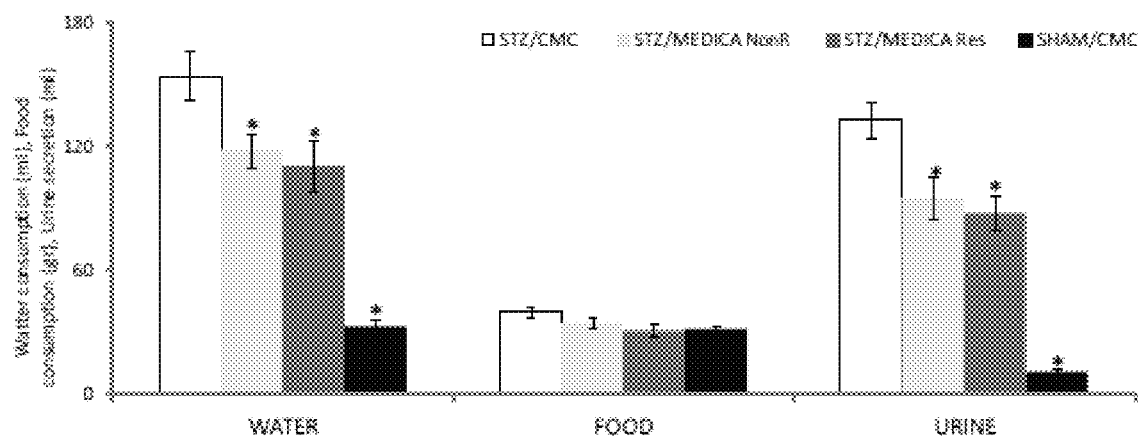
Figure 1D:
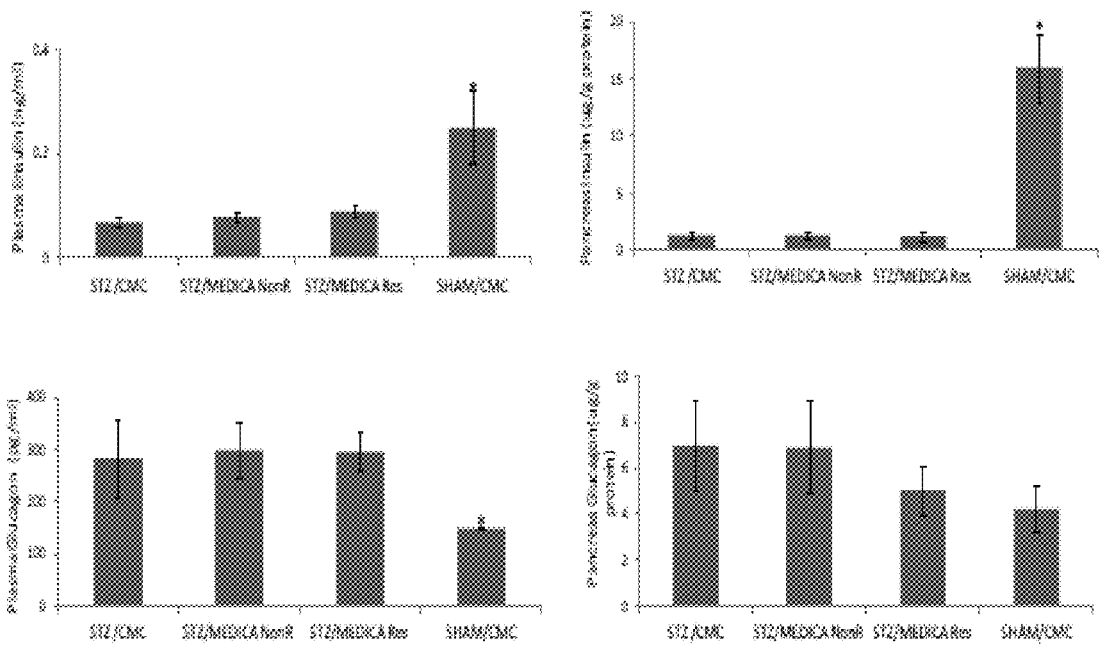

Of note, administering MEDICA16αα to SHAM (control) non-diabetic rats did not result in hypoglycemia (FIG. 1A). Normalizing the FBG in STZ/MEDICA Res rats was also accompanied by an amelioration in blood glucose level as demonstrated in an i.p glucose tolerance test (IPGTT) (FIG. 1B), with partial decrease in fluid consumption and excretion (FIG. 1C).

The response to MEDICA16αα in STZ diabetic rats was not accounted for by differences in measured plasma MEDICA16αα exposures between responsive and non-responsive rats (22.5±4.4 and 26.0±8.7 ng MEDICA16αα/ml plasma, respectively, data not shown). Also, the response was not accounted for by significant increase in pancreatic and/or plasma insulin, neither by significant decrease in glucagon content, as apparent from the results shown in FIG. 1D. Without being bound to theory, the results presented above imply that MEDICA16αα efficacy was not associated with improving the pancreatic beta- and/or alpha-cell status.

Example 2 Effect of MEDICA16αα in Combination with Insulin on STZ Diabetic Rats

The all-or-none response of STZ diabetic rats to MEDICA16αα shown in Example 1 above may reflect minor individual variability in residual endogenous pancreatic and/or plasma insulin content. Therefore, the effect of administering a combination of MEDICA16αα and sub-therapeutic insulin was examined in STZ diabetic rats, as detailed below.

Figure 2A:
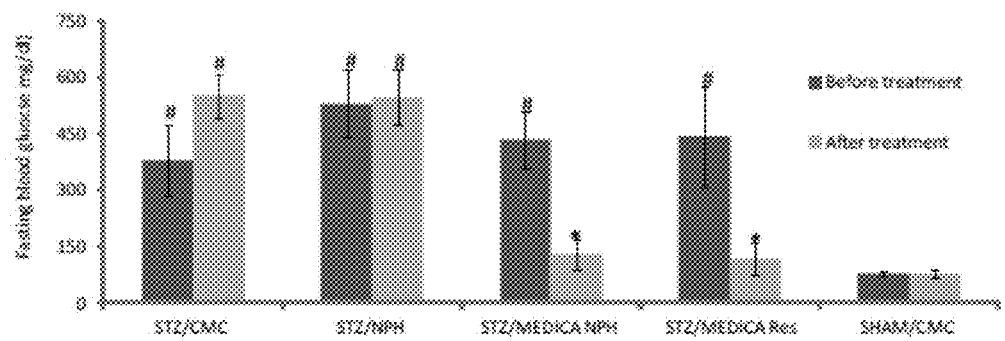
FIGS. 2A-2D. Anti-diabetic efficacy of MEDICA16αα/NPH insulin in STZ diabetic rats. STZ diabetic rats (FBG >300 mg/dl) were treated with CMC for 15 consecutive days or with oral MEDICA16αα(15 mg/kg b.i.d) for five consecutive days. MEDICA16αα-responsive rats were further treated with MEDICA16αα(15 mg/kg b.i.d) for 10 consecutive days ("STZ/MEDICA Res"). MEDICA16αα non-responsive rats (FBG >250 mg/dl) were further treated for 10 consecutive days with either insulin Neutral Protamine Hagedorn (NPH) (3 u/kg b.i.d s.c.) ("STZ/NPH"), or with insulin NPH (3 u/kg b.i.d s.c) in combination with MEDICA16αα(15 mg/kg b.i.d) ("STZ/MEDICA NPH"). "SHAM/CMC" were SHAM rats treated with CMC for 15 consecutive days.

As shown in FIG. 2A, treating STZ diabetic animals with a combination of a sub-therapeutic dose of Neutral Protamine Hagedorn NPH insulin (3 u/kg body weight, s.c, twice per day (b.i.d)) with oral (as an add-on) MEDICA16αα(15 mg/kg body weight, twice per day under the conditions described above), resulted in normalizing FBG in all (100%) STZ/MEDICA NonR animals, similar to the results obtained for the STZ rats that were responsive to treatment with MEDICA16αα("STZ/MEDICA Res").

Figure 2B:
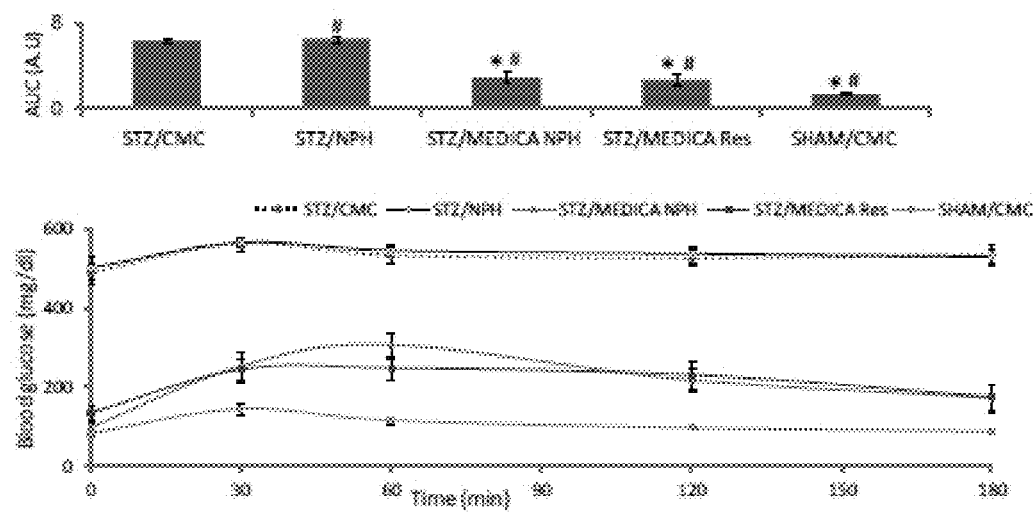
Figure 2C:
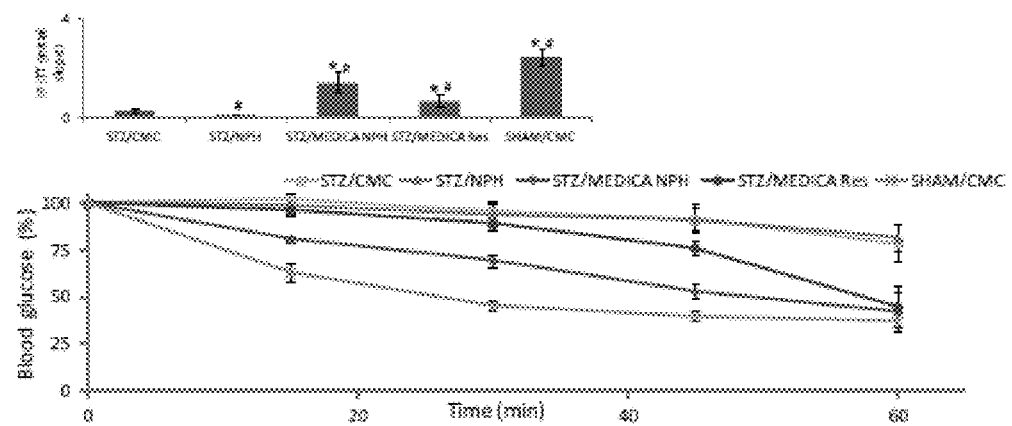
Figure 2D:
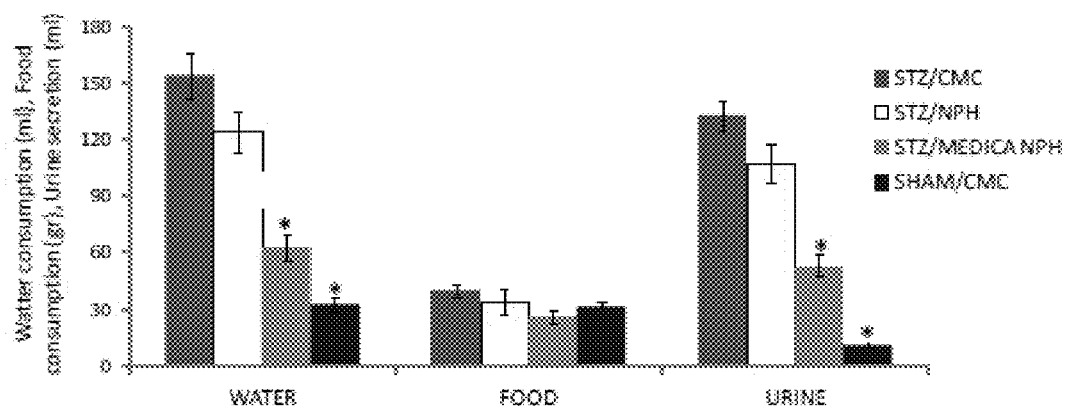

This effect of the combination treatment was accompanied by an amelioration in blood glucose level in the i.p glucose tolerance test (IPGTT) test (as shown in FIG. 2B) and in the i.p. insulin tolerance test (IPITT), as shown in FIG. 2C. In line with that, as demonstrated in FIG. 2D, the combined treatment resulted in significant decrease in fluid consumption and urination.

Of note, the concerned sub-therapeutic dose of insulin NPH was without any effect in controlling glycemia in STZ diabetic rats (the fasting blood glucose level, the IPGTT and the IPITT profiles of rats treated only with sub-therapeutic dose of insulin NPH were similar to the respective characteristics of non treated STZ diabetic rats, as shown in FIGS. 2A, B, C), implying a requirement for the combined MEDICA16αα/insulin treatment.

Glycemic control of STZ diabetic rats by the combined MEDICA16αα/insulin treatment was not accounted for by increase in MEDICA16αα exposure due to add-on insulin (data not shown). Also, the combined treatment did not result in increase in pancreatic or plasma insulin, or decrease in glucagon (data not shown), implying that responsiveness of STZ diabetic rats to MEDICA16αα/insulin was not accounted for by modulating total body exposures to insulin or glucagon.

Figure 3A:
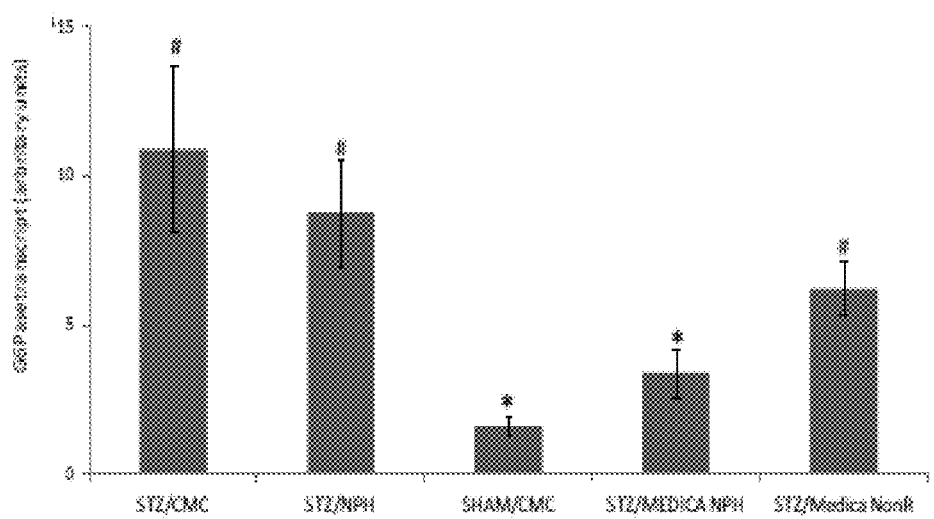
FIGS. 3A-3E. Suppression of hepatic gluconeogenesis by MEDICA16αα in STZ diabetic rats. STZ diabetic rats (FBG >300 mg/dl) were treated under the conditions described in FIG. 2. Mean±SE (n=8-10 per group). *Significant as compared with STZ/CMC rats (P<0.05). #Significant as compared with SHAM/CMC rats (P<0.05). Inset-representative blots.
Figure 3A:
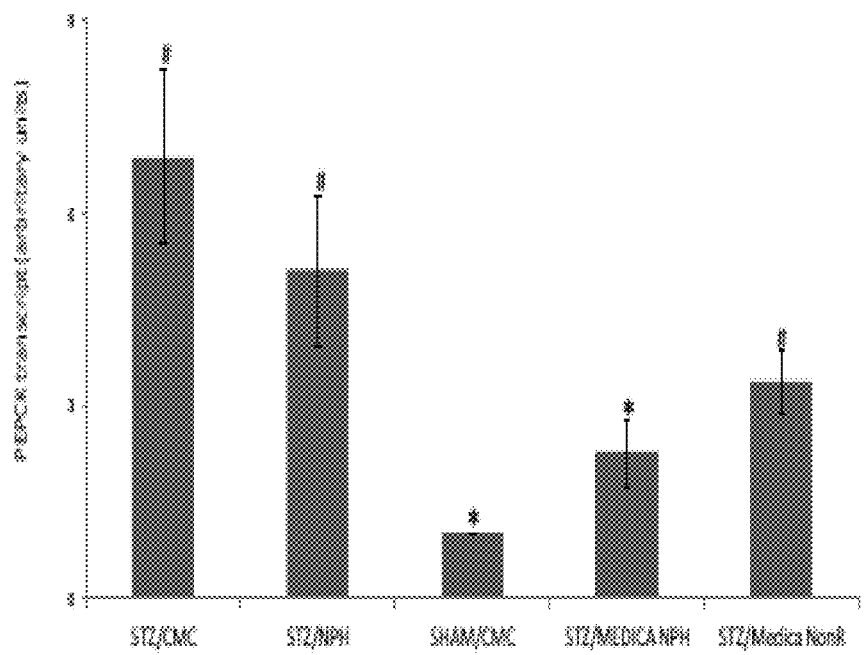

Example 3 A Combination of MEDICA16αα and Insulin Affect Hepatic Gluconeogenesis and Glucose Production in STZ Diabetic Rats Since FBG is mainly controlled by hepatic glucose production (HGP), MEDICA16αα efficacy in normalizing FBG was further verified in terms of modulating hepatic gluconeogenesis. As shown in FIG. 3A, treatment of STZ diabetic rats with MEDICA16αα as add-on to sub-therapeutic insulin resulted in robust suppression of glucose-6-phosphatase and PEPCK transcripts to levels observed in SHAM/CMC rats (FIG. 3A).

That is in contrast to rats treated with sub-therapeutic insulin alone (termed "STZ/NPH"), where the respective transcripts remained essentially unaffected as compared to their level in the STZ control group (termed "STZ/CMC", FIG. 3A).

The insulin-sensitizing activity of MEDICA16αα was further pursued in terms of hepatic transcription factors that induce the expression of gluconeogenic genes, namely, CREB and CRTC2 (29). CREB transcriptional activity is activated by its Ser179 phosphorylation by cAMP-activated protein kinase A (PKA), while CRTC2 transcriptional activity is suppressed by its Ser171 phosphorylation by AMP-activated protein kinase (AMPK), resulting in its nuclear exclusion and degradation.

Figure 3B:
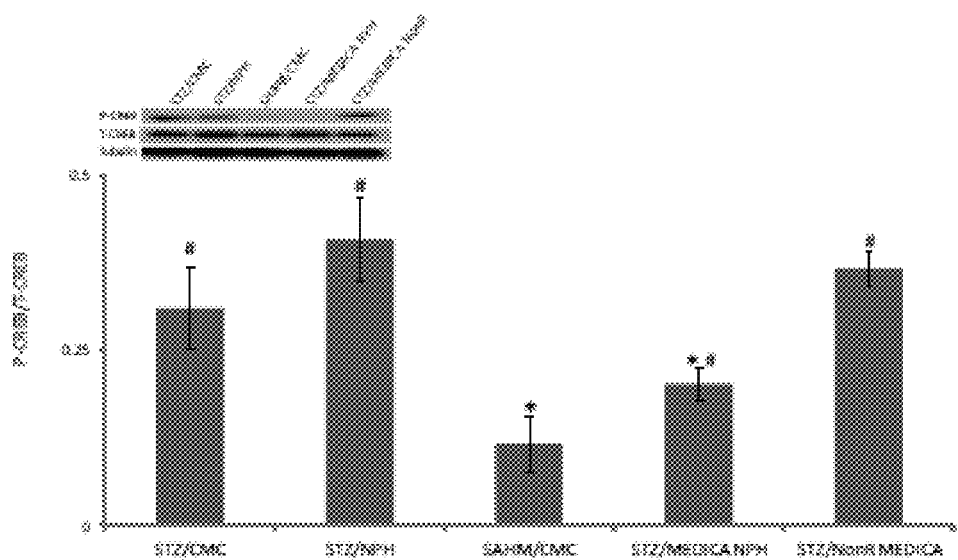
Figure 3C:
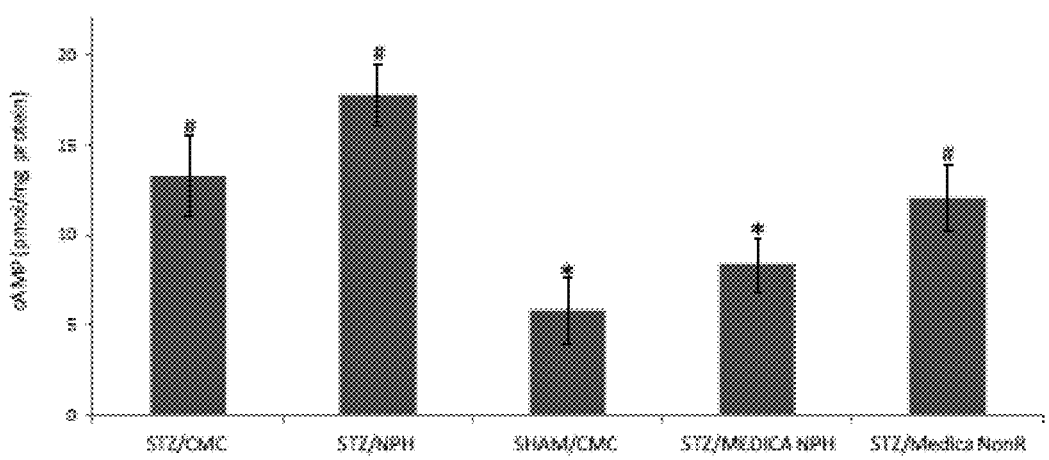

MEDICA16αα/insulin (as a combination) treatment resulted in suppressing CREB(Ser179) phosphorylation to levels similar to those observed in SHAM rats, whereas treatment with sub-therapeutic insulin alone was ineffective, as shown in FIG. 3B. Suppression of phospho-CREB (Ser179) by MEDICA16αα was accounted for by suppressing hepatic cAMP levels, as demonstrated in FIG. 3C, in line with our previous studies whereby MEDICA16ββ was reported to inhibit adipose adenylate cyclase (30).

Figure 3D:
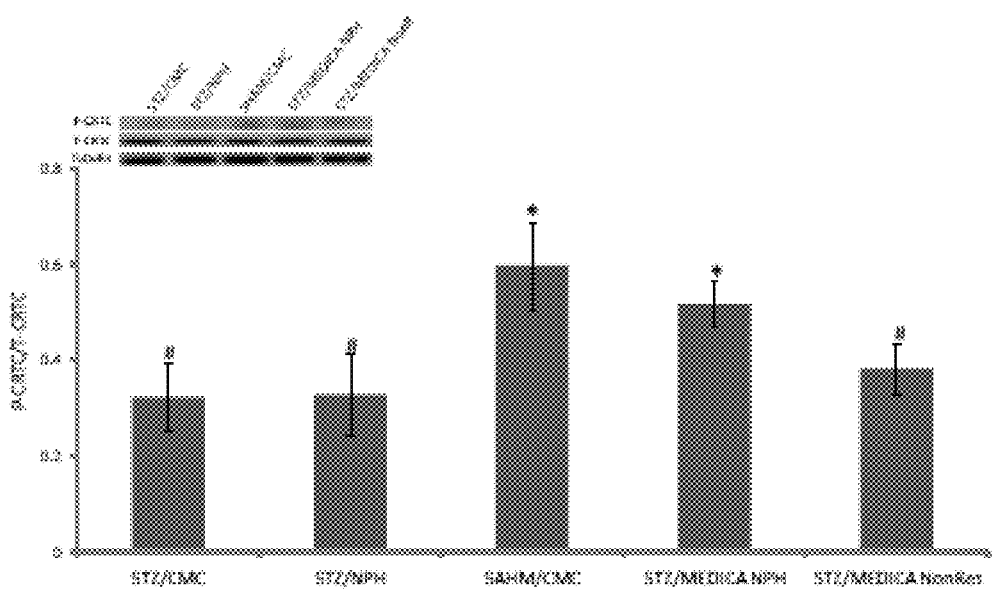
Figure 3E:
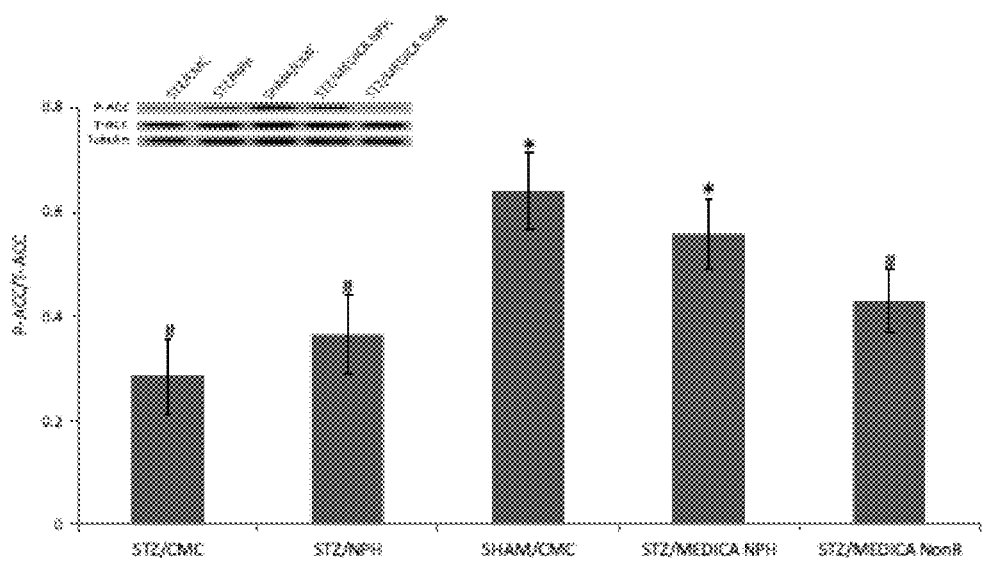

In addition to inhibiting CREB, as shown in FIG. 3D, MEDICA16αα/insulin treatment, but not a sub-therapeutic amount of insulin, resulted in phosphorylating CRTC2 (Ser171), being accounted for by MEDICA16αα-activated AMPK (25), as reflected by phosphorylation of its downstream ACC(Ser79) substrate (FIG. 3E).

Hence, without being bound by theory, suppression of hepatic gluconeogenesis by MEDICA16αα/insulin may be ascribed to suppression of hepatic CREB and CRTC2 transcriptional activities, being mediated by suppressing the adenylate cyclase and by activating AMPK, respectively.

MEDICA16αα/insulin efficacy in ameliorating the IPGTT and IPITT (namely lowering blood glucose level) may indicate that in addition to suppressing hepatic glucose production (HGP), the combined treatment may induce an increase in total body glucose uptake due to peripheral sensitization to insulin.

Figure 4A:
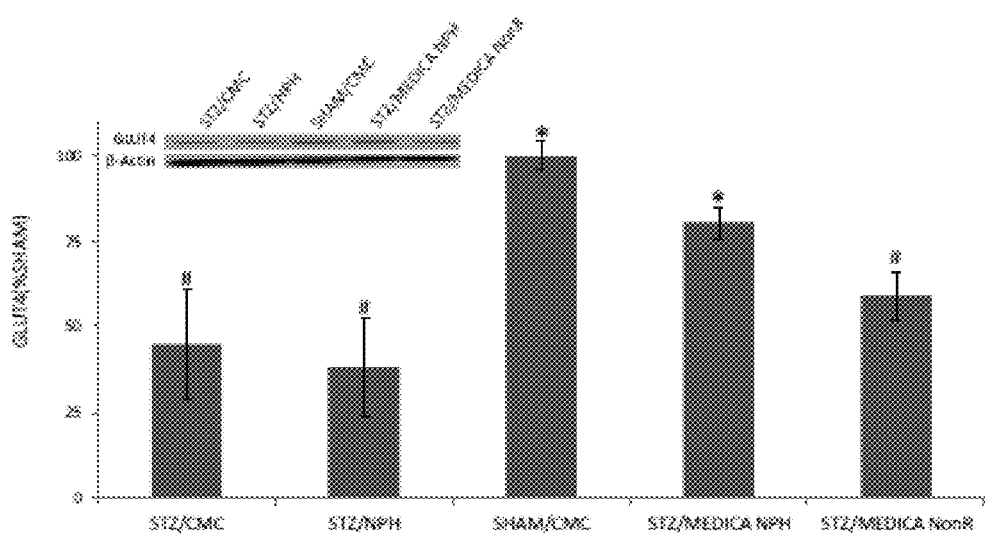
FIGS. 4A-4E. Activation of Soleus GLUT4 by MEDICA16αα in STZ diabetic rats. STZ diabetic rats (FBG >300 mg/dl) were treated under the conditions described in FIG. 2. Mean±SE (n=6 per group). *Significant as compared with STZ/CMC rats (P<0.05). #Significant as compared with SHAM/CMC rats (P<0.05).
Figure 4B:
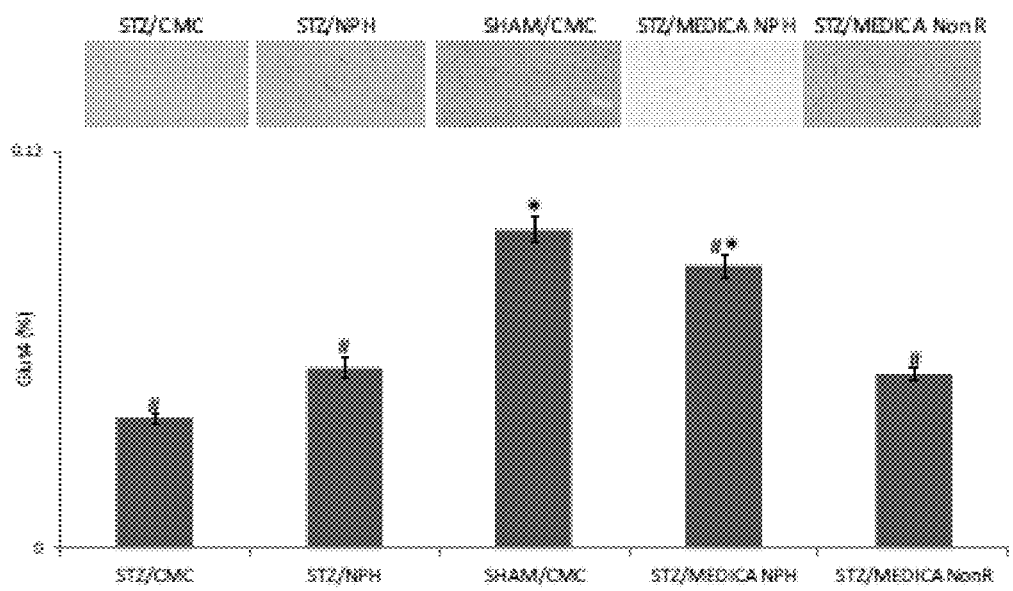
Figure 4C:
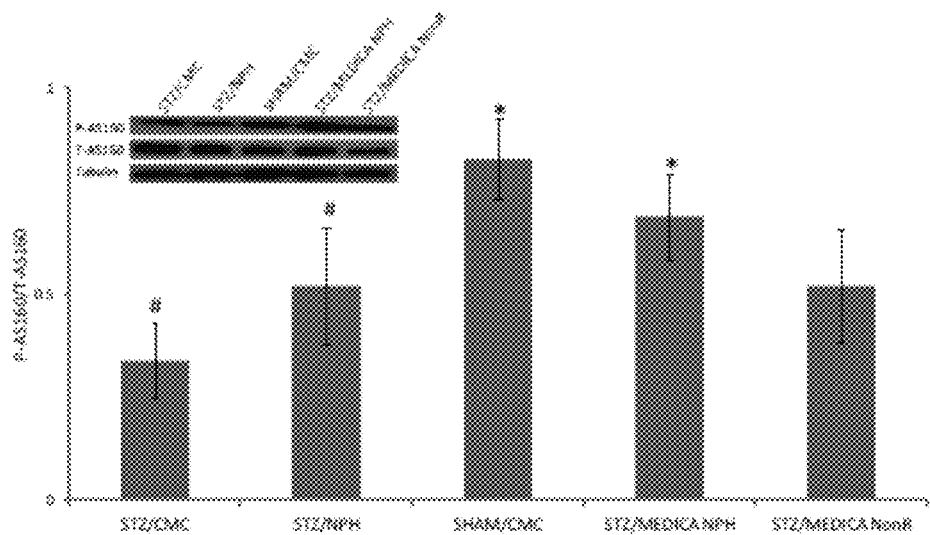
Figure 4D:
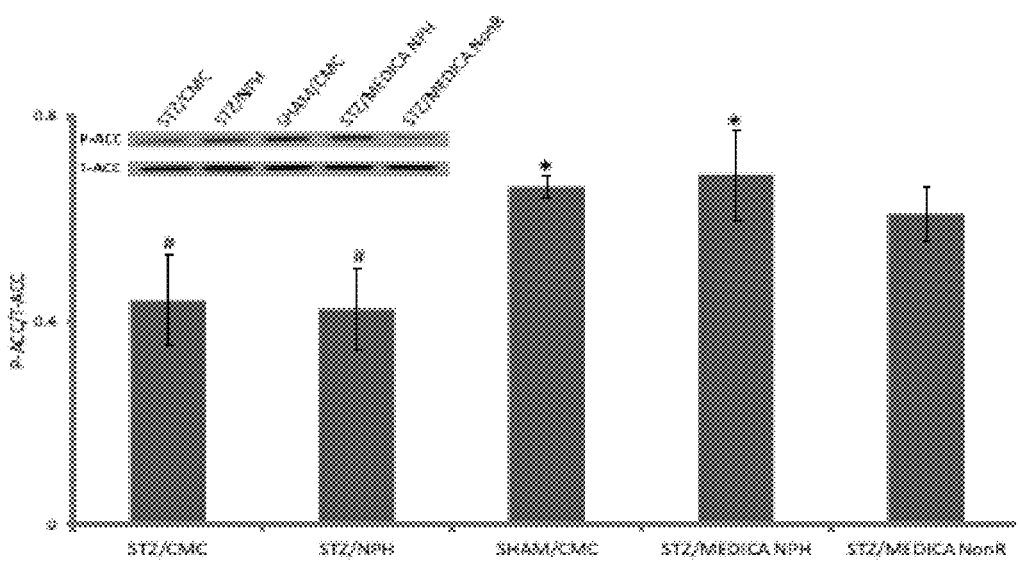
Figure 4E:
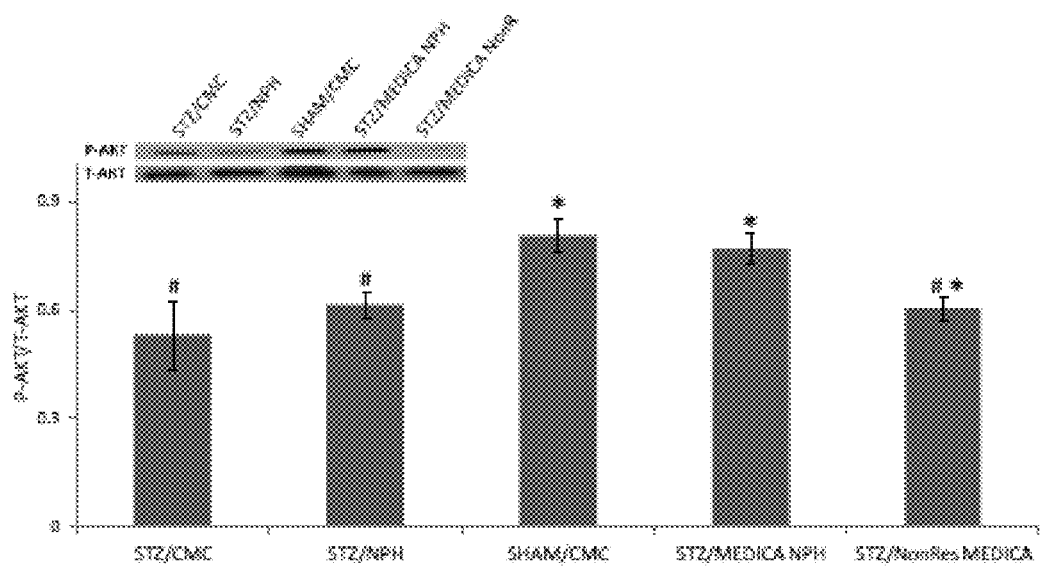

Indeed, MEDICA16αα/insulin treatment of STZ diabetic rats, but not sub-therapeutic insulin, resulted in increase in soleus glucose transporter type 4 (GLUT4) expression, as shown in FIG. 4A, with enrichment in soleus sarcolemma GLUT4 content (FIG. 4B). MEDICA16αα-induced soleus GLUT4 was accounted for by increase in phosphorylated AS160(Thr642) (FIG. 4C), being driven by activated AMPK (FIG. 4D) and AKT (FIG. 4E) (31).

Example 4 MEDICA16αα Effects in Non-Obese Diabetic (NOD) Mice

MEDICA efficacy in modulating the development of autoimmune type 1 diabetes (T1D) has been further evaluated in NOD mice. The NOD mouse model relates to the gradual development of autoimmune T1D, whereby the anti-beta cell autoimmune reaction results first in a prediabetic beta-cell insulitis normo-glycemic phase, being followed with time by total beta-cell loss with concomitant overt diabetes.

Figure 5B:
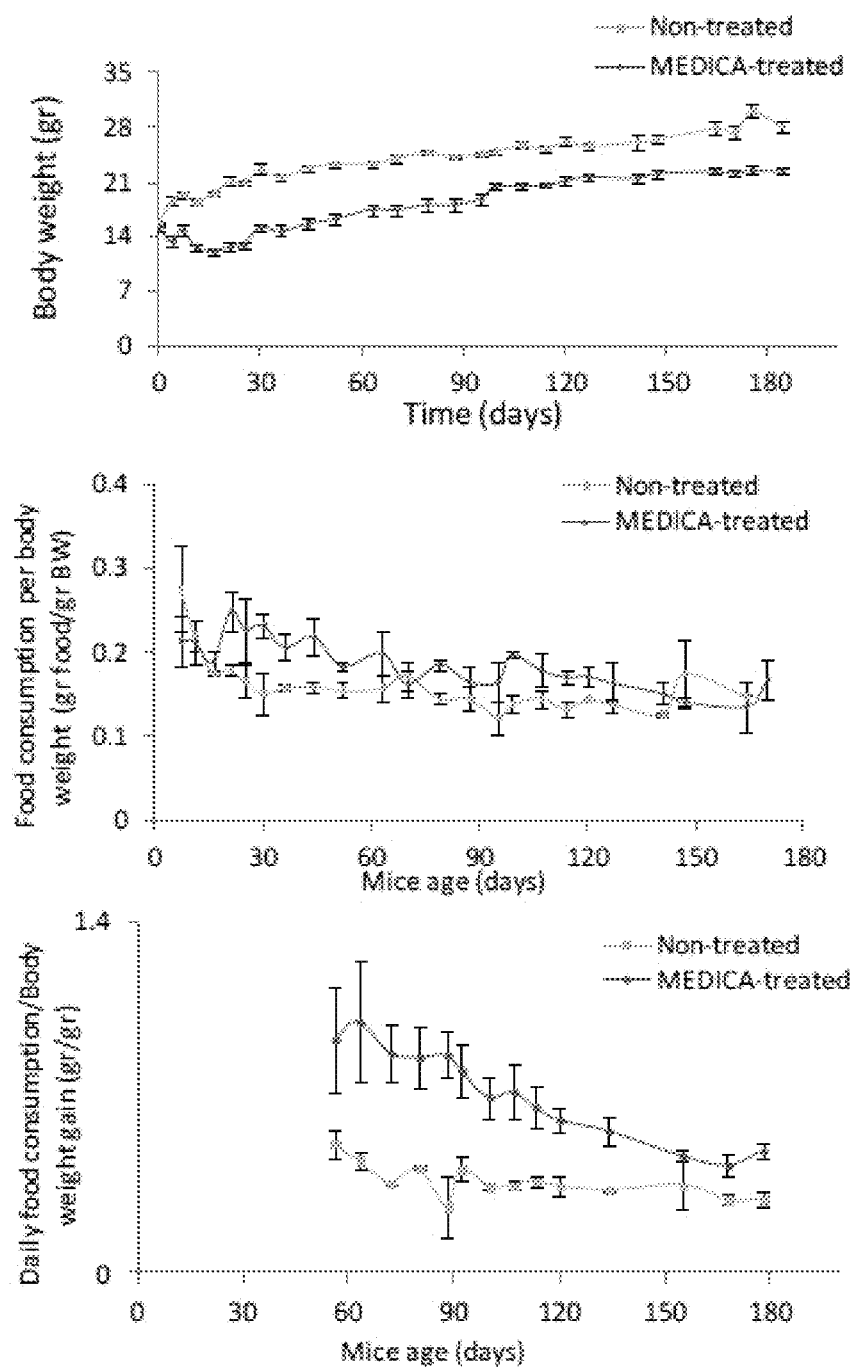

As shown in FIG. 5A, treatment of NOD mice with oral MEDICA16αα(at 40 mg/kg per day, as a single treatment and as described above) for 21 weeks, from weaning on, resulted in delaying or preventing the development of T1D in 71% of NOD mice, as compared with 32% of mice in the non-treated group. MEDICA16αα treatment was accompanied by 40% decrease in body weight gain, in face of a relative increase in food consumption (FIG. 5B).

Insulitis is an inflammation of the islets of Langerhans of the pancreas, being infiltrated by polymorphonuclear leukocytes and mononuclear cells, leading to loss of beta-cell mass. Interestingly, MEDICA16αα efficacy in preventing or delaying T1D was not accounted for by affecting the islet insulitis score of pre-diabetic NOD mice. As demonstrated in FIG. 6A, the insulitis rankings of MEDICA16αα-treated and non-treated NOD mice were essentially similar, with some non-significant improvement in the rank 1 grade in MEDICA16αα-treated NOD mice.

MEDICA16αα efficacy in preventing or delaying T1D in NOD mice was however accompanied by normalizing the pre-diabetic IPGTT profile of 14-week and 24-week old NOD mice, while glucose-stimulated plasma insulin remained unaffected (FIG. 6B and FIG. 6C), implying sensitization to insulin by MEDICA16αα treatment.

Figure 7A:
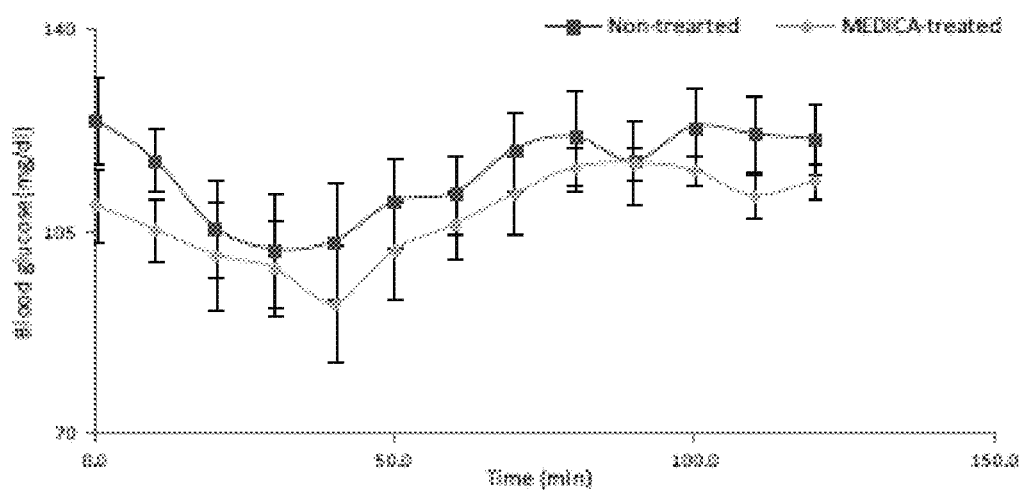
FIGS. 7A-7F. MEDICA16αα-induced sensitization to insulin in NOD mice. NOD mice were treated under the conditions described in FIG. 5. MEDICA16αα-treated and non-treated 12-week old NOD mice were subjected to hyperinsulinemic euglycemic clamp. Mean±SE (n=7 per group). *Significant as compared with non-treated mice (P<0.05).
Figure 7B:
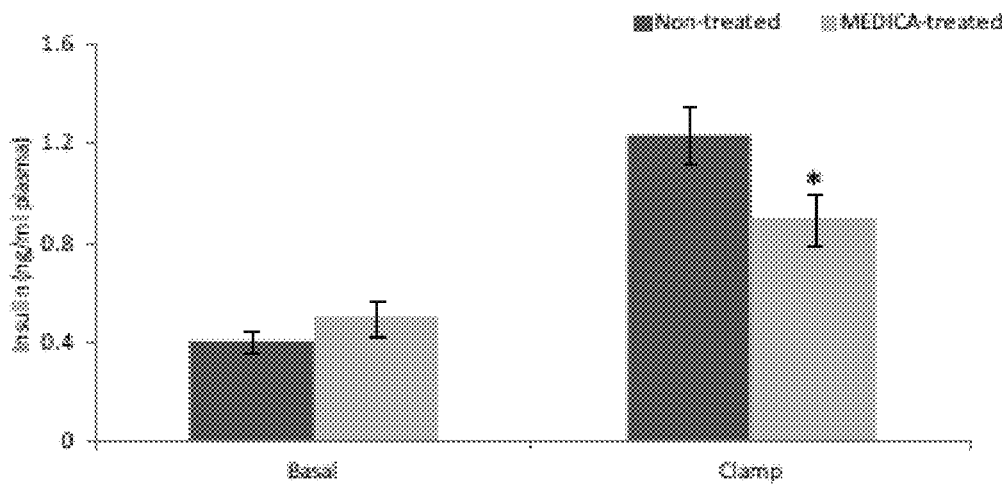

Sensitization to insulin by MEDICA16αα treatment was further verified by performing hyperinsulinemic-euglycemic clamp studies carried out in 14-week old pre-diabetic NOD mice (FIG. 7A and FIG. 7B).

The hyperinsulinemic-euglycemic clamp (also referred to as "insulin clamp") is widely considered as the gold standard method for assessing insulin action in vivo. During an insulin clamp, hyperinsulinemia is achieved by a constant insulin infusion. Euglycemia is maintained via a concomitant glucose infusion at a variable rate. This variable glucose infusion rate (GIR) is determined by measuring blood glucose at brief intervals throughout the experiment and adjusting the GIR accordingly. The GIR is indicative of whole-body insulin action, as mice with enhanced insulin action require a greater GIR. The insulin clamp can incorporate administration of isotopic deoxyglucose to assess tissue-specific glucose uptake, and isotopic glucose to assess the ability of insulin to suppress the rate of endogenous glucose appearance (endoRa), a marker of hepatic glucose production.

Figure 7C:
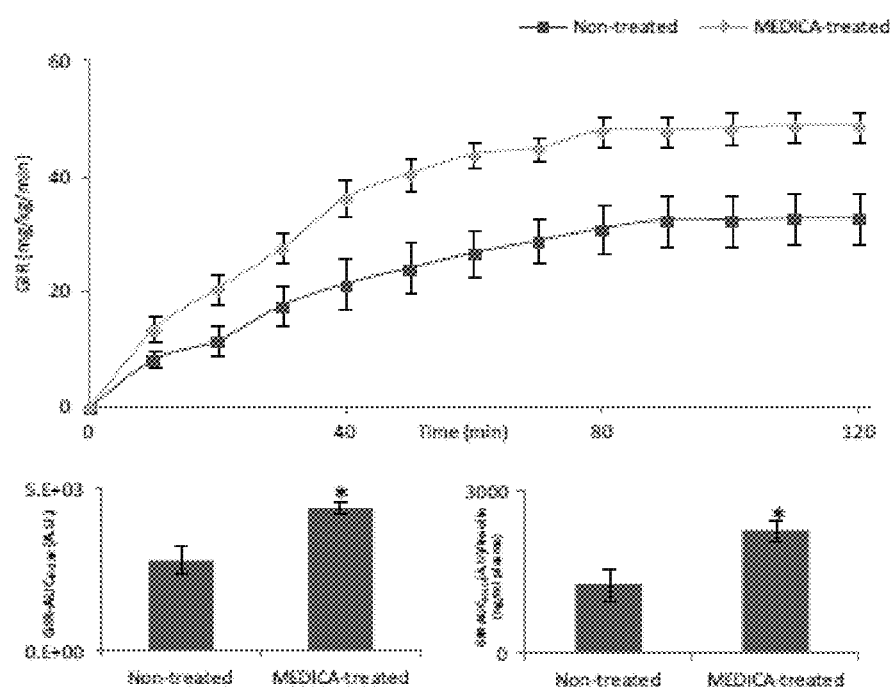
Figure 7D:
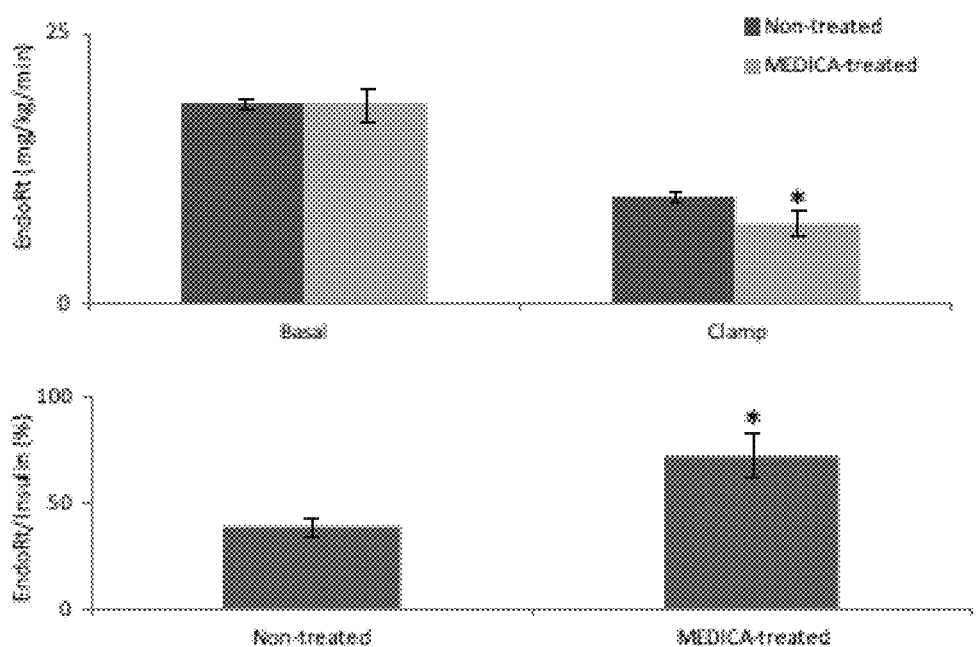
Figure 7E:
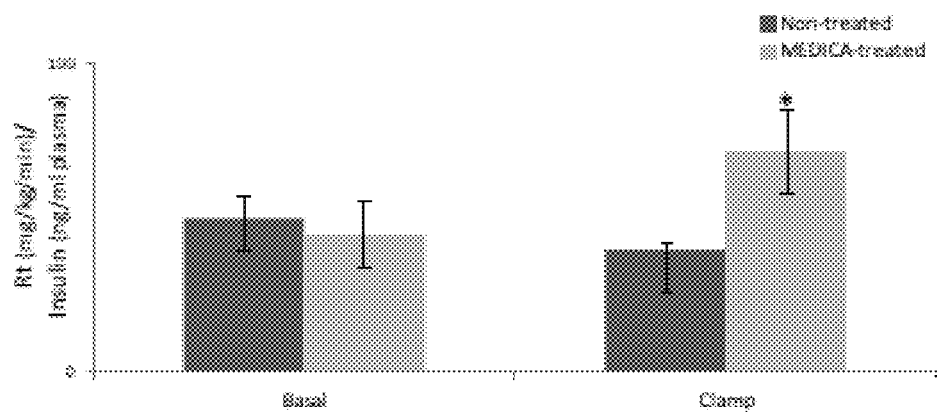
Figure 7F:
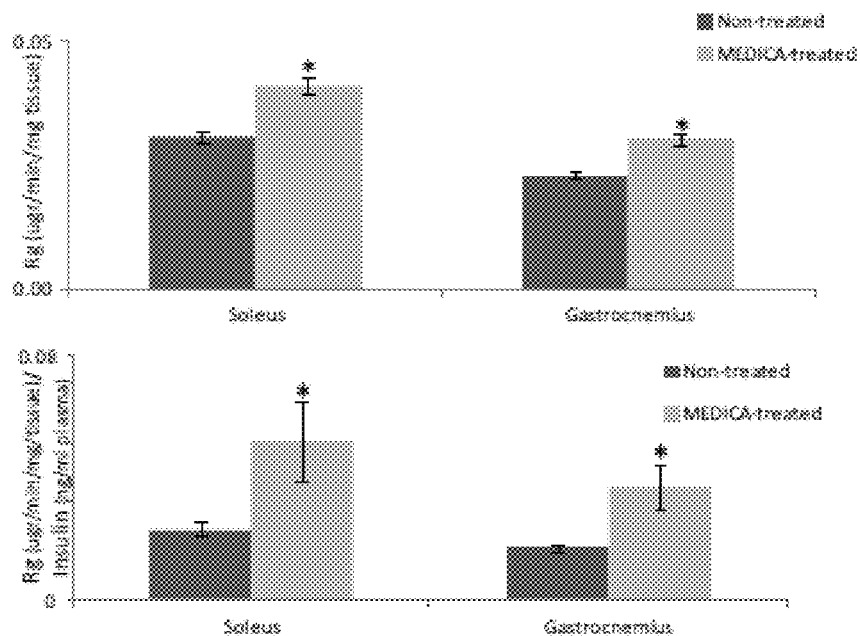

As demonstrated in FIG. 7C, MEDICA16αα treatment resulted in 37% increase in glucose infusion rate (GIR), being further accentuated by the decrease in clamped plasma insulin in MEDICA16αα-treated mice. Total body sensitization to insulin was accounted for by hepatic sensitization to insulin as reflected by the insulin-induced decrease in endogenous glucose production, being further accentuated by the decrease in clamped plasma insulin in MEDICA16αα-treated NOD mice (FIG. 7D). Sensitization to insulin was further evident by MEDICA16αα-induced increase in total body glucose turnover (FIG. 7E), and further verified by insulin-induced deoxyglucose uptake into soleus and gastrocnemius muscles of MEDICA16αα treated NOD mice (FIG. 7F).

The invention claimed is:

1. A method of treatment of type 1 diabetes (T1D) in a subject in need thereof, wherein said subject is administered with standard of care doses of insulin or an insulin analogue, said method comprising administering to said subject a therapeutically effective amount of a compound of the general formula (I):

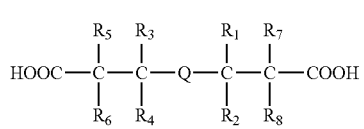

(I)

or a pharmaceutically acceptable salt, ester, amide, anhydride or lactone thereof, wherein (a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure,
wherein administration of said compound of general formula (I) reduces the standard of care administered dose of insulin or insulin analogue and
wherein administration of said compound of general formula (I) reduces the fasting blood glucose level and/or the HbA1c level in said subject.

2. A method for reducing the standard of care administered dose of insulin or an insulin analogue, or for obviating the need for administration of insulin or an insulin analogue in a type 1 diabetic (T1D) subject in need thereof, said method comprising administering to said subject a therapeutically effective amount of a compound of the general formula (I):

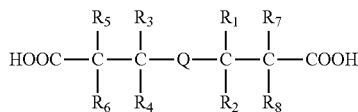

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure,
wherein administration of said compound of general formula (I) reduces the standard of care administered dose of insulin or insulin analogue, or obviates the need for administration of insulin or an insulin analogue to said subject, and
wherein administration of said compound of general formula (I) also reduces the fasting blood glucose level and/or the HbA1c level in said subject.

3. A method of treating type 1 diabetes (T1D) in a subject diagnosed as having T1D by the presence of one or more autoantibody associated with T1D, wherein said subject is not administered with insulin or an insulin analogue, wherein said method comprises administering to said subject a therapeutically effective amount of a compound of the general formula (I):

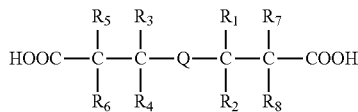

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure,
wherein administration of said compound of general formula (I) reduces the fasting blood glucose level and/or the HbA1c level in said subject.

4. A method of preventing or delaying the onset of insulin or an insulin analogue treatment in a T1D subject diagnosed as having T1D by the presence of one or more autoantibody associated with T1D, and wherein said subject is not administered with insulin or an insulin analogue, said method comprising administering to said subject a therapeutically effective amount of a compound of the general formula (I):

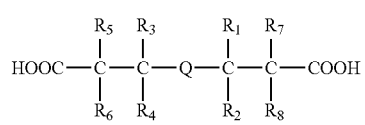

or a pharmaceutically acceptable salt, ester, amide, anhydride or lactone thereof, wherein
(a) each of $R_1$-$R_4$ is independently an unsubstituted or substituted hydrocarbyl and each of $R_5$-$R_8$ is independently hydrogen, hydroxyl, lower alkyl, lower alkoxy or trifluoromethyl; or
(b) each of $R_5$-$R_8$ is independently an unsubstituted or substituted hydrocarbyl and each of $R_1$-$R_4$ is hydrogen;
wherein Q is a diradical of a linear chain of 6 to 14 carbon atoms, one or more of which may be replaced by heteroatoms selected from N, P, O and S, said chain is optionally substituted with hydroxyl, lower alkyl, or lower alkoxy, and one or more of said carbon or heteroatom chain members optionally forming a part of a ring structure.

5. The method according to claim 3, wherein said subject was diagnosed as having blood glucose levels and/or HbA1c level below the standard of care threshold requiring administration of insulin or an insulin analogue.

6. The method according to claim 3, wherein said at least one antibody associated with T1D is selected from the group consisting of islet cell autoantibodies, autoantibodies to insulin, autoantibodies to GAD, autoantibodies to tyrosine phosphatase and autoantibodies to the Zn transporter.

7. The method according to claim 1, wherein said compound is comprised in a pharmaceutical composition together with at least one pharmaceutically acceptable excipient or carrier.

8. The method according to claim 1, wherein said compound is administered at a therapeutically effective amount of about 5 mg to about 200 mg per subject per day.

9. The method according to claim 1, wherein said compound is administered at a therapeutically effective amount of about 5 mg to about 100 mg per subject per day.

10. The method according to claim 1, wherein said compound is administered at a therapeutically effective amount of about 0.05 mg/kg to about 3.0mg/kg per day.

11. The method according to claim 1, wherein said compound is administered once or twice daily, or once, twice or thrice weekly.

12. The method according to claim 1, wherein said compound is administered orally.

13. The method according to claim 1, wherein said compound is administered in a unit dosage form.

14. The method according to claim 1, wherein in said compound of formula (I), Q represents a straight polymethylene chain $(CH_2)_n$, wherein n is an integer of from 6 to 14.

15. The method according to claim 1, wherein in said compound of formula (I) said hydrocarbyl is selected from the group consisting of an optionally substituted alkyl, alkenyl, alkynyl and cycloalkyl group, an optionally substituted aryl, and an optionally substituted aralkyl.

16. The method according to claim 15, wherein said alkyl is a short-chain alkyl group of 1 to 4 carbon atoms.

17. The method according to claim 1, wherein said compound is a compound of the formula (II):

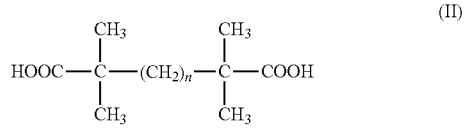

where n is an integer from 10 to 16, or a pharmaceutically acceptable salt, ester, amide, anhydride or lactone thereof.

18. The method according to claim 17, wherein said compound of formula (II) is any one of 2,2,15,15-tetramethylhexadecane-1,16-dioic acid (referred to herein as M16αα), or 2,2,17,17-tetramethyloctadecane-1,18-dioic acid (referred to herein as M18αα) and 2,2,19,19-tetramethyleicosa-1,20-dioic acid (referred to herein as M20αα).

19. The method according to claim 17, wherein said compound of formula (II) is 2,2,15,15tetramethylhexadecane-1,16-dioic acid (referred to herein as M16αα).

20. The method according to claim 1, wherein said compound is a compound of the formula (III):

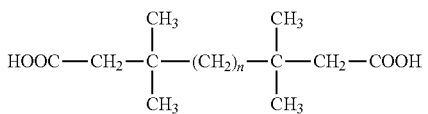

wherein n is an integer of from 8 to 14, or a pharmaceutically acceptable salt, ester, amide, anhydride or lactone thereof.

21. The method according to claim 20, wherein said compound of formula (III) is any one of 3,3,14,14-tetramethylhexadecane-1,16-dioic acid (referred to herein as M16ββ), or 3,3,16,16-tetramethyloctadecane-1,18-dioic acid (referred to herein as M18ββ) and 3,3,18,18-tetramethyleicosa-1,20-dioic acid (referred to herein as M20ββ).

22. The method according to claim 1, wherein said salt is a salt with an inorganic or organic cation, said ester is a lower alkyl ester; said amide is a mono- and di-substituted; said anhydride is an anhydride with a lower alkanoic acid; and/or said lactone is formed by ring closure of either or both carboxylic groups with a free hydroxy substituent (or substituents) in the compound of formula (I).

23. The method according to claim 13, wherein said unit dosage form is a capsule or a tablet.

24. the method according to claim 22, wherein said salt is an alkali metal salt, an alkaline earth metal salt, an ammonium salt or a substituted ammonium salt.

25. The method according to claim 4, wherein said compound of formula (I) is any one of 2,2,15,15-tetramethylhexadecane-1,16-dioic acid (referred to herein as M16αα), or 2,2,17,17-tetramethyloctadecane-1,18-dioic acid (referred to herein as M18αα) and 2,2,19,19-tetramethyleicosa-1,20-dioic acid (referred to herein as M20αα).

26. The method according to claim 16, wherein said alkyl is a methyl group.

* * * * *